(12) United States Patent
Fazenda et al.

(10) Patent No.: US 10,655,155 B2
(45) Date of Patent: May 19, 2020

(54) BIOPROCESS FOR COPRODUCTION OF ETHANOL AND MYCOPROTEINS

(71) Applicant: UNIVERSITY OF STRATHCLYDE, Glasgow (GB)

(72) Inventors: Mariana Fazenda, Cambridge (GB); Craig Johnston, Glasgow (GB); Brian McNeil, Glasgow (GB)

(73) Assignee: UNIVERSITY OF STRATHCLYDE, Glasgow (GB)

( * ) Notice: Subject to any disclaimer, the term of this patent is extended or adjusted under 35 U.S.C. 154(b) by 0 days.

(21) Appl. No.: 15/518,952

(22) PCT Filed: Oct. 21, 2015

(86) PCT No.: PCT/GB2015/053145
§ 371 (c)(1),
(2) Date: Apr. 13, 2017

(87) PCT Pub. No.: WO2016/063053
PCT Pub. Date: Apr. 28, 2016

(65) Prior Publication Data
US 2017/0226551 A1 Aug. 10, 2017

(30) Foreign Application Priority Data
Oct. 22, 2014 (GB) .................................. 1418739.7

(51) Int. Cl.
C12P 21/00 (2006.01)
C12P 7/06 (2006.01)
C12P 7/14 (2006.01)
A23K 10/38 (2016.01)

(52) U.S. Cl.
CPC .............. *C12P 21/00* (2013.01); *A23K 10/38* (2016.05); *C12P 7/06* (2013.01); *C12P 7/065* (2013.01); *C12P 7/14* (2013.01); *C12P 2203/00* (2013.01); *Y02E 50/17* (2013.01); *Y02P 60/873* (2015.11)

(58) Field of Classification Search
None
See application file for complete search history.

(56) References Cited

U.S. PATENT DOCUMENTS

| | | | |
|---|---|---|---|
| 4,447,534 A | | 5/1984 | Moebus et al. |
| 4,782,024 A | | 11/1988 | Scott et al. |
| 2003/0044951 A1 | | 3/2003 | Sporleder et al. |
| 2007/0231869 A1 | | 10/2007 | Holmgren et al. |
| 2010/0178675 A1 | | 7/2010 | Lawton et al. |
| 2016/0312247 A1* | | 10/2016 | Lennartsson ........... C12P 7/065 |

FOREIGN PATENT DOCUMENTS

| | | |
|---|---|---|
| CN | 101691539 | 4/2010 |
| CN | 103039699 | 4/2013 |
| EP | 0058426 | 2/1982 |
| WO | WO2009/079183 | 6/2009 |
| WO | WO2014/014682 | 1/2014 |
| WO | WO2014/020142 | 2/2014 |

OTHER PUBLICATIONS

Rachael Link "Mycoprotein: Beneficial Vegetarian Protein Source or Dangerous Allergen" Apr. 22, 2018, 8 pgs (Year: 2018).*
ODonnell "Molecular Phylogenetic, Morphological, and Mycotoxin Data Support Reidentification of the Quorn Mycoprotein Fungus as *Fusarium venenatum*" Fungal Genetics and Biology 23, 57-67 (1998) (Year: 1998).*
Suihko et al. "The Production of Ethanol From D-Glucose and D-Xylose by Different Fusarium Strains" Biotechnology Letters vol. 3 No. 12 723-728 (1981) (Year: 1981).*
Wiebe et al. "Myco-protein from Fusarium venenatum : a well-established product for human consumption" Appl Microbiol Biotechnol (2002) 58:421-427 (Year: 2002).*
Silva et al., "Using the residue of spirit production and bio-ethanol for protein production by yeasts," Waste Management, vol. 31, Issue 1, 2011, 108-114.
Third Party Observations filed in EP App. No. 15790186.9 filed 2019 in the EPO pp. 1-4.
Trinci, "'Quorn' Mycoprotein," Mycologist, 1991, 5, pp. 106-109.
Moore, et al., "21st Century Guide Book to Fungi" 2018, Alcoholic Fermentations, pp. 1-5.
Wikipedia, "Fusarium Venenatum," 2019, pp. 1-3.
Ratpukdi, et al. "Ethanol production potential from fermented rice noodle waste water treatment using entrapped yeast cell sequencing batch reactor," Applied Water Sci., 2012, 2, pp. 47-53.
Anderson, et al., "Primary Metabolism and Biomass production from Fusarium" 2011, Applied Mycology of Fusarium, pp. 1-10.
Trinci, et al., "Myco-Protein: A twenty-year overnight success story," Mycol. Res. 1991, 96, pp. 1-13.
EPO Statement on non-relevance of the Third Party Observations for EP15790186 pp. 1.
Cardona, C. et al., "Fuel ethanol production: Process design trends and integration opportunities," Bioresource Technology, 2007, 98, 2415-2457.
Sigma-Aldrich Enzyme Datasheet for alpha-amylase, 1 page.
Sigma-Aldrich Enzyme Datasheet for A7420, 1 page.
Finn, B. et al., "Near-infrared spectroscopic monitoring of biomass, glucose, ethanol and protein content in a high cell density baker's yeast fed-batch bioprocess," Yeast, 2006, 23, 507-517.
Gadonna-Widehem, P.I et al., "A laboratory protocol for determining glucose and maximum ethanol production from wheat grain: application to a complete genetic set of near-isogenic waxy lines," Journal of Agricultural and Food Chemistry, 2012, 60, 985-990.
Mycroprotein GRAS Application, GRN No. 91, 2001, 74 pages.
Panagiotopoulos, I.A., et al., "Fermentative hydrogen production from pretreated biomass: A comparative study," Bioresource Technology, 2009, 100, 6331-6338.

(Continued)

*Primary Examiner* — Thane Underdahl
(74) *Attorney, Agent, or Firm* — Barnes & Thornburg LLP

(57) ABSTRACT

The present invention relates to the co-production and isolation of mycoprotein and ethanol from carbohydrate feedstock material (e.g cereals). The present invention also provides a fermentation system for the co-production of mycoprotein from a carbohydrate feedstock material.

9 Claims, 18 Drawing Sheets

(56) References Cited

OTHER PUBLICATIONS

PCT Search Report and Written Opinion for PCT/GB2015/053145, completed Dec. 16, 2015, 11 pages.
Ferreira, Jorge A., et al., "Production of Ethanol and Biomass from Thin Stillage Using Food-Grade Zygomycetes and Ascomycetes Filamentous Fungi," 2014, Energies. vol. 7, No. 6, pp. 3872-3885.
Rasmussen M. L., et al., "Water Reclamation and Value-Added Animal Feed from Corn-Ethanol Stillage by Fungal Processing," 2014, Bioresource Technology. vol. 151, pp. 284-290.

* cited by examiner

BIOPROCESS FOR COPRODUCTION OF ETHANOL AND MYCOPROTEINS

CROSS-REFERENCE TO RELATED APPLICATIONS

This application is a national stage entry under 35 USC § 371 of PCT International Application PCT/GB2015/053145, filed 21 Oct. 2015, which claims priority to United Kingdom Patent Application Serial No.: 1418739.7, filed 22 Oct. 2014, the entire disclosure of each is expressly incorporated by reference herein.

FIELD OF THE INVENTION

The present invention relates to the co-production and isolation of mycoprotein and ethanol from carbohydrate feedstock material (e.g cereals). The present invention also provides a fermentation system for the co-production of mycoprotein from a carbohydrate feedstock material.

BACKGROUND TO THE INVENTION

Livestock farming satisfies the rapidly growing consumer driven demand for meat and dairy products and utilises approximately 70% of total global agricultural land for grazing and feed crop production. However, growing population and changing dietary preferences for meat and dairy will place increasing demand on global agricultural land.

Biotechnology offers some potential for meat substitutes to be produced more efficiently with lower environmental impact. The notable example is Mycoprotein (Quorn) produced by aerobic fermentation of glucose syrup. It is currently marketed as a (relatively expensive) healthy vegetarian alternative. It's relatively high cost is associated with use of refined feedstock (glucose syrup) and high fixed costs associated with investment cost in a dedicated modest capacity plant and energy costs associated with aerobic fermentation.

Livestock feed largely comprises of cereals (maize, wheat) providing the majority of carbohydrate, combined with protein enhancement (main source soymeal) to enhance the protein content for optimal nutrition. Approx 40% of grains are used as livestock feed. Agricultural yield of soybeans is typically significantly lower than cereals.

Fermentation from grain feedstock typically converts carbohydrates leaving a distiller dried grains with solubles (DDGS) residue concentrated in protein. This is used as a high protein component in livestock feed, however it's relatively low digestibility limits its mix ratio.

Global bioethanol production exceeds 60 million tepa, the 2 major sources being fermentation of cereals (particularly US maize converting approx 40% of its production) and Brazilian sugarcane. The economics (excluding government incentives) and environmental benefits of bioethanol from cereals (maize/wheat) are marginal. There are significant political issues associated with food v fuel pressures on land use and energy security.

U.S. Pat. No. 4,447,534 describes a process of producing ethanol using yeast where control of the growth conditions can increase the yield of the yeast and hence yeast derived unicellular protein.

Silva et al (Waste Management, 31 (2011), 108-114) describes a method of utilising the residue of spirit production and bio-ethanol for protein production by yeasts, such as *Saccharomyces cerevisiae* and *Candida parapsilosis*. The single cell protein form the yeast may be used as a source of supplemental protein for animal feed.

WO2009/079183 describes a process for improving the nutritional quality of a feed spent waste product which remains after fermentation of grain to produce alcohol. The spent waste product may be fermented with a microbe which is capable of breaking down cellulose and/or hemicellulose to one or more sugars and in turn using the sugar(s) to proliferate. As the microbes contain protein their proliferation serves to increase the protein content of the spent waste product. A variety of microbes including bacteria, yeasts and fungi are described, but there is no teaching of providing any single cell protein in isolation of the spent waste product.

It would be desirable to be able to provide a system which can be adapted to be able to produce both mycoprotein and ethanol in isolation of other material, whilst optionally being capable of varying the amount of each co-product based upon desired requirements, such as prevailing economic and/or socio-economic concerns.

It is amongst the object of the present invention to provide a method for the production, optionally co-production, of isolated mycoprotein and/or ethanol.

SUMMARY OF THE INVENTION

In a first aspect there is provided an integrated system capable of producing and isolating mycoprotein derived from filamentous fungi and ethanol from a carbohydrate feedstock.

The carbohydrate feedstock may be a mixed or single feedstock.

It will be appreciated from the above that the order of mycoprotein and ethanol production can be swapped, such that ethanol can be produced before the mycoprotein and vice versa. However, in a preferred embodiment of the present invention mycoprotein is produced initially, followed by ethanol. As mentioned above, the methods and systems of the present invention are integrated and controllable in terms of the amount of mycoprotein or ethanol which can be produced. Through appropriate control of the substrate used to obtain the mycoprotein or ethanol and growth conditions, especially oxygen content, it is possible to vary, in a controllable manner, the amount of mycoprotein or ethanol produced. Thus, for example, depending on prevailing commercial requirements, it is possible to vary the ratio of mycoprotein to ethanol which is produced in accordance with the invention. This may be achieved manually, semi-automatically or fully automatically. For example, in an automatic or semi-automatic process a user may indicate or input into a user programmable interface, for example, the desired mycoprotein to ethanol ratio and the system can then control the substrate flux and growth conditions in order to achieve the required mycoprotein to ethanol ratio.

Mycoprotein, as referred to herein is understood to be a form of single cell protein specifically produced by filamentous fungi, such as *Fusarium* species including *Fusarium venenatum*.

The single feedstock may comprise a plurality of metabolisable substrates, typically carbohydrate containing substrate(s). Preferably the feedstock comprises one or more cereal materials. The present system may be differentiated from non-integrated systems which may require separate feedstocks being provided for a mycoprotein producing process and an ethanol producing process.

Mycoprotein may be obtained through aerobic digestion of a substrate material. Ethanol may be produced through anaerobic fermentation of a substrate material, although optionally there may be an initial period of aerobic digestion in order to allow growth of the microorganism(s) which are capable of generating ethanol during anaerobic digestion.

In one embodiment the microorganism(s) for use in producing mycoprotein and ethanol are different. In such an embodiment the microorganism(s) capable of producing mycoprotein is a *Fusarium* species, such as *Fusarium venenatum* and the microorganism(s) capable of producing ethanol are a *Saccharomyces* species, such as *Saccharomyces cerevisiae*. The inventors have observed that is it possible for a single type of microorganism to be capable of producing both mycoprotein and thereafter ethanol. Thus, in one embodiment the integrated method of the invention employs a single type of microorganism to produce both mycoprotein and ethanol. Such a single type of microorganism may be a *Fusarium* species such as *F. venenatum*, or multiple species.

In a further aspect there is provided an integrated method for the co-production of mycoprotein and ethanol from a cereal material, the method comprising the steps of:
a) providing an aqueous fermentable broth comprising one or more cereal materials;
b) fermenting at least a portion of the aqueous fermentable broth with a micro-organism(s) in order to obtain mycoprotein or ethanol respectively and partially fermented broth;
c) separating/isolating the mycoprotein or ethanol from the partially fermented broth;
d) fermenting at least a portion of the partially fermented broth, optionally with a portion of unfermented aqueous fermentable broth, with a micro-organism(s) in order to obtain ethanol or mycoprotein respectively and a spent fermentation residue; and
e) isolating the ethanol or mycoprotein from the spent fermentation residue.

Said partially fermented broth may be derived from an initial fermentation broth which has undergone an initial fermentation in order to produce mycoprotein or ethanol. The partially fermented broth is capable of being fermented in order to produce the second product, namely ethanol or mycoprotein, depending on what has been produced first.

It will be appreciated from the above that the order of mycoprotein and ethanol production can be swapped, such that ethanol can be produced before the mycoprotein and vice versa. However, in a preferred embodiment of the present invention mycoprotein is produced initially, followed by ethanol.

The methods of the present invention can be carried out in a batch, continuous or semi-continuous manner.

The method may further comprise the step of separating the spent fermentation residue (also known as stillage) to obtain a wet solids fraction and a soluble fraction. The soluble fraction can be concentrated and the resulting syrup may be combined with the wet solids fraction, which may be dried in order to obtain a material known as Dried Distillers Grains with Solubles (DDGS).

Typically said one or more cereal materials may include wheat, maize (corn), barley, rice, sorghum, buckwheat, oats, rye and the like. The cereal may be of food grade quality or may in fact be material which is no longer suitable for human consumption. One of the aforementioned examples may be used, or mixtures comprising two or more types of cereals may be employed in the present invention. The present invention is not intended to be limited by the type or types of cereals which may be employed and this may simply be dictated by prevailing economic and/or geographical and hence availability considerations at the time.

The one or more cereal materials may be subjected to a milling, grinding and/or cutting process in order to break the cereal material down into smaller fragments and also potentially to release some of the proteins, sugars and other materials which may be present in the cereal. The broken down material may be mixed with water to a concentration of for example 170-500 to 50 g/L and the pH adjusted as necessary, in order to provide the fermentation broth.

Any starch which may be present in the fermentation broth may be subjected to hydrolysation or partial hydrolysation by employing one or more of gelatinization, liquefaction and/or saccharification. Starch is found in nature as insoluble, non-dispersible granules resistant to enzymic breakdown. Gelatinisation is the swelling of the starch granule in the presence of heat and water. At this point, the starch or ground cereal slurry thickens considerably and would be difficult to process if an alpha-amylase were not added to partially hydrolyse the starch to dextrins. A dextrin containing solution is generally much more fluid or liquefied. The alpha-amylase serves to reduce the viscosity of the solution and also to produce a lower molecular size substrate. A lower molecular size substrate molecule is desired for the efficient action of glucoamylase which hydrolyses the dextrins to glucose.

Enzymes such as alpha-amylase and glucoamylase may be added in order to break down or hydrolyse the starch which is present. The alpha-amylase is a bacterial thermostable endo-amylase. It hydrolyses $\alpha$-1,4 bonds at random points in the starch molecule to rapidly reduce the viscosity of gelatinised starch solutions. This enzyme is a metal ion-containing protein and requires a small amount of calcium ion during use for maximum activity and stability. The enzyme cannot hydrolyse $\alpha$-1,6 bonds but can bypass these branch points in amylopectin. The product of the reaction is dextrins—short glucose chains, and small amounts of glucose and maltose.

Glucoamylase, produced by fungi, is an exo-amylase. It hydrolyses the maltose and dextrins from the non-reducing end of the molecule. Glucoamylase hydrolyses both $\alpha$-1,4 and $\alpha$-1,6 bonds to completely degrade the dextrins to glucose. The enzyme is optimally active at pH 3.5-4.5. Typically alpha-amylase may be added at a concentration of 0.25-1.5% w/w of the solid material and glucoamylase may be added at a concentration of 0.25-3% w/w of the solid material. Following the enzyme digestions, the fermentation broth may be subjected to a heat treatment in order to destroy the enzymes and kill any bacteria which may be present and which could interfere with subsequent process steps.

However, the addition of enzymes, adjustment of pH and heating and cooling which is necessary adds to the cost dramatically and can therefore be undesirable. The inventors have observed that microorganisms such as *Fusarium venenatum* (*F. venenatum*) can undergo fermentation with unhydrolysed cereal grain starch solution. As conventional mycoprotein production generally requires glucose as a starting carbon source, it was surprising that material which had not been subjected to starch hydrolysis could be used to make mycoprotein. This could lead to considerable costs savings when carrying out the present process without necessarily having to carry out the liquefaction and/or saccharification steps.

Mycoprotein production is carried out using a filamentous fungus such as *F. venenatum* to ferment material within the fermentable broth. As mentioned above hydrolysis of starch may or may not be carried out prior to the fermentation being carried out. An appropriate source of nitrogen and nutrients, such as Vogel salts, may be provided for effective mycoprotein fermentation (approximately 1-L of Vogel salts supplemented with 40 g of glucose). This may be added prior to and/or during fermentation.

It may be desirable to include an anti-foaming agent during the fermentation in order to minimise any foaming which may occur due to, for example, proteins present in the fermentation broth. For example rapeseed oil may be added at a concentration up to 1% (v/v). Not only can this serve as an anti-foaming agent, but the rapeseed oil can also be used as a carbon source and hence can be fermented. It may only be necessary to add an anti-foaming agent, such as rapeseed oil, at the beginning of the fermentation.

As an aerobic fermentation process, production of mycoprotein requires the addition of a source of oxygen as either air or oxygen. Together with the control of other fermentation conditions the extent of aeration will influence the relative conversion of carbohydrate to mycoprotein and ethanol and can be used to influence the conversion ratio. The integrated process producing both products (mycoprotein and ethanol) allows operating conditions which do not require the minimisation of ethanol (which would be a waste byproduct in conventional mycoprotein fermentation) during mycoprotein fermentation. Conditions favouring mycoprotein/ethanol production could be selectively altered in modes of either sequential or phased operation. Desirably operating conditions could be phased to match the extent of more energy intensive aerobic fermentation to mycoprotein with energy supply phasing to match daily energy cycles of renewable energy availability.

Mycoprotein and/or ethanol fermentations may be carried out as batch, semi-continuous, or continuous processes. A continuous process may offer advantage in an ability to maintain optimal steady state control conditions and interface with continuous separation processes. Once completed, the mycoprotein and spent fermentation broth may be subjected to a heat treatment in order to remove/destroy nucleic acid, such as RNA, which may be present. The mycoprotein may then be separated/isolated from the spent fermentation broth, such as by centrifugation or filtering, for example and then dried. The dried mycoprotein material may then be further processed in order to provide a suitable food grade material. Spent mycoprotein fermentation liquors (combined with separated starch hydrolysate and/or separated protein/fibre solids) can be further fermented for ethanol production. *S. cerevisiae* may be used in order to ferment the material and produce ethanol. A typical process is described in Finn et al. (2006).

Once fermentation has been carried out and ethanol produced, it is necessary to separate/isolate the ethanol from the other material which is present. This may be achieved through a continuous distillation process as described for example in (Cardona and Sanchez, 2007). This provides a high purity of ethanol, which can be further purified by passing through a molecular sieve, for example, in order to remove water and further concentrate the ethanol.

Non-ethanol containing material which is removed during the distillation process includes solids and soluble material which is typically called stillage. This solids and soluble material may be separated by pressing or centrifugation, for example, in order to provide a wet solids material and a liquid. The wet solids material may be further dried and the liquid may be concentrated in order to provide a syrup. The dried solid and syrup may be used separately, or combined in order to provide a material known as Dried Distillers Grains with Solubles (DDGS).

It can be seen that the present invention provides a process which is capable of converting a relatively low grade/value material into mycoprotein, which can be used as a human food source; ethanol, which can be used as a biofuel; and spent material, such as DDGS, which can be used as an animal feed.

DETAILED DESCRIPTION

The present invention will now be further described by way of non-limiting examples and with reference to the figures which show:

Figure 1:
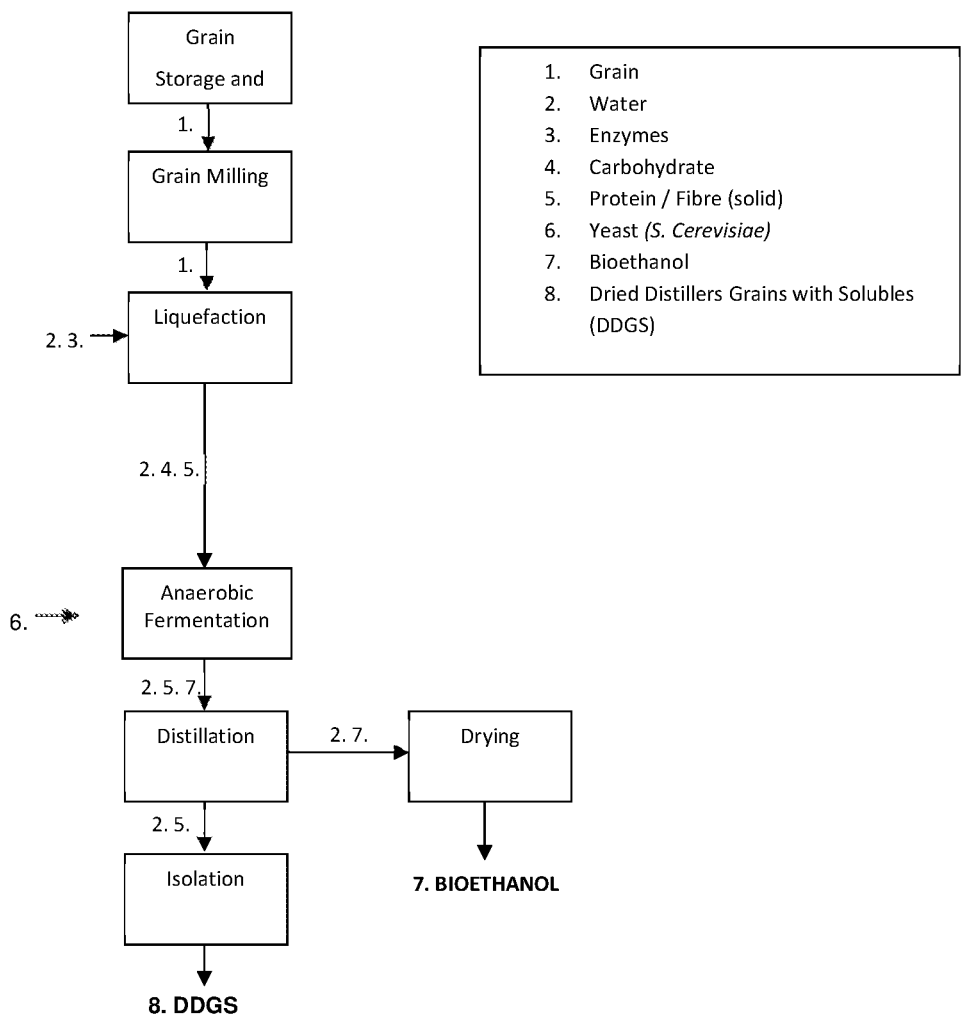
FIG. 1 shows in schematic flow diagram from a typical configuration of an existing method for ethanol production.

FIG. 1—Flow diagram of typical configuration of existing method for ethanol production.

Figure 2:
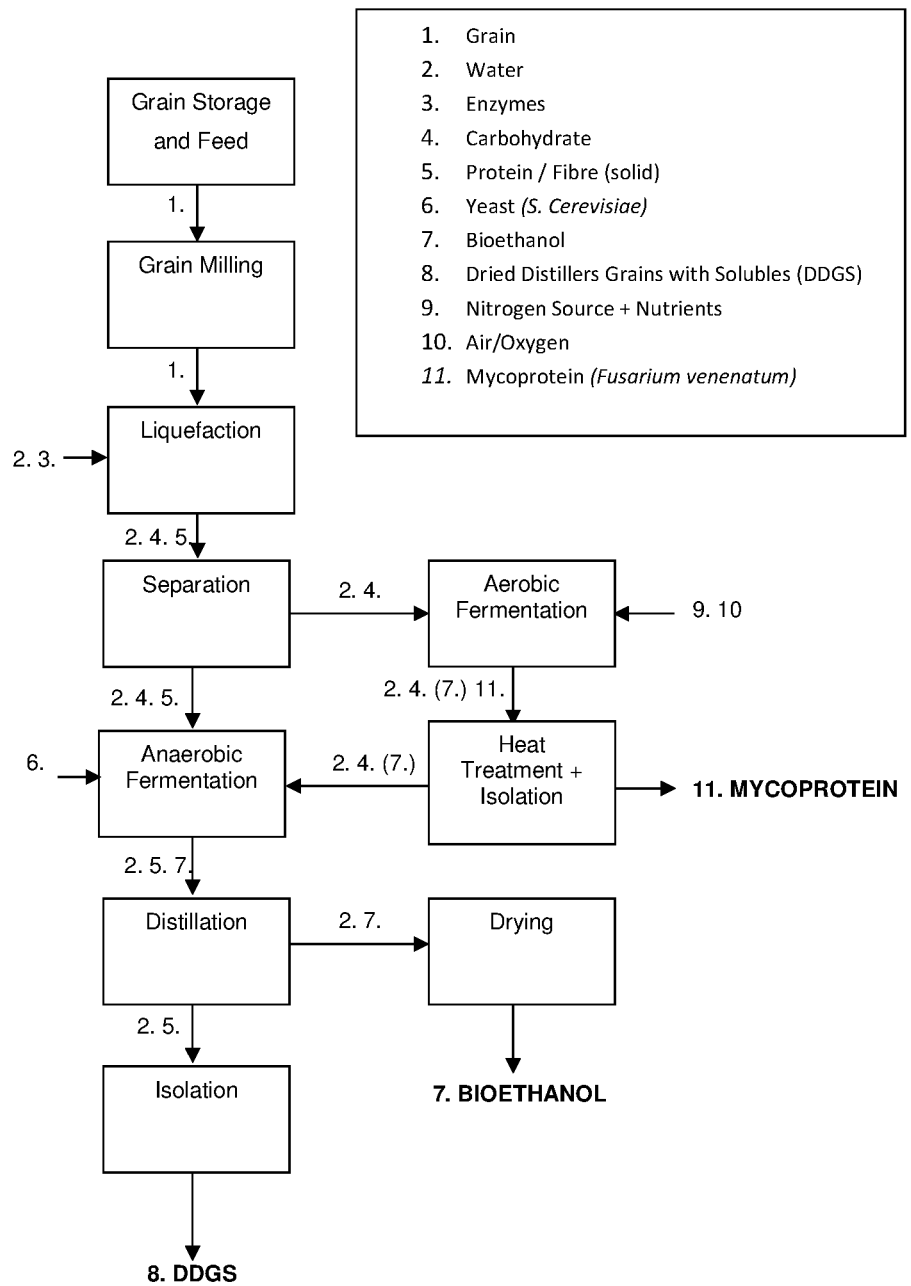
FIG. 2 to FIG. 8 show in schematic flow diagram from a number of example system configurations in accordance with the present invention whereby mycoprotein and ethanol can be co-produced from a grain feedstock.

FIG. 2—Flow diagram of an integrated configuration of co-production method for mycoprotein and ethanol production using two microorganisms.

Figure 3:
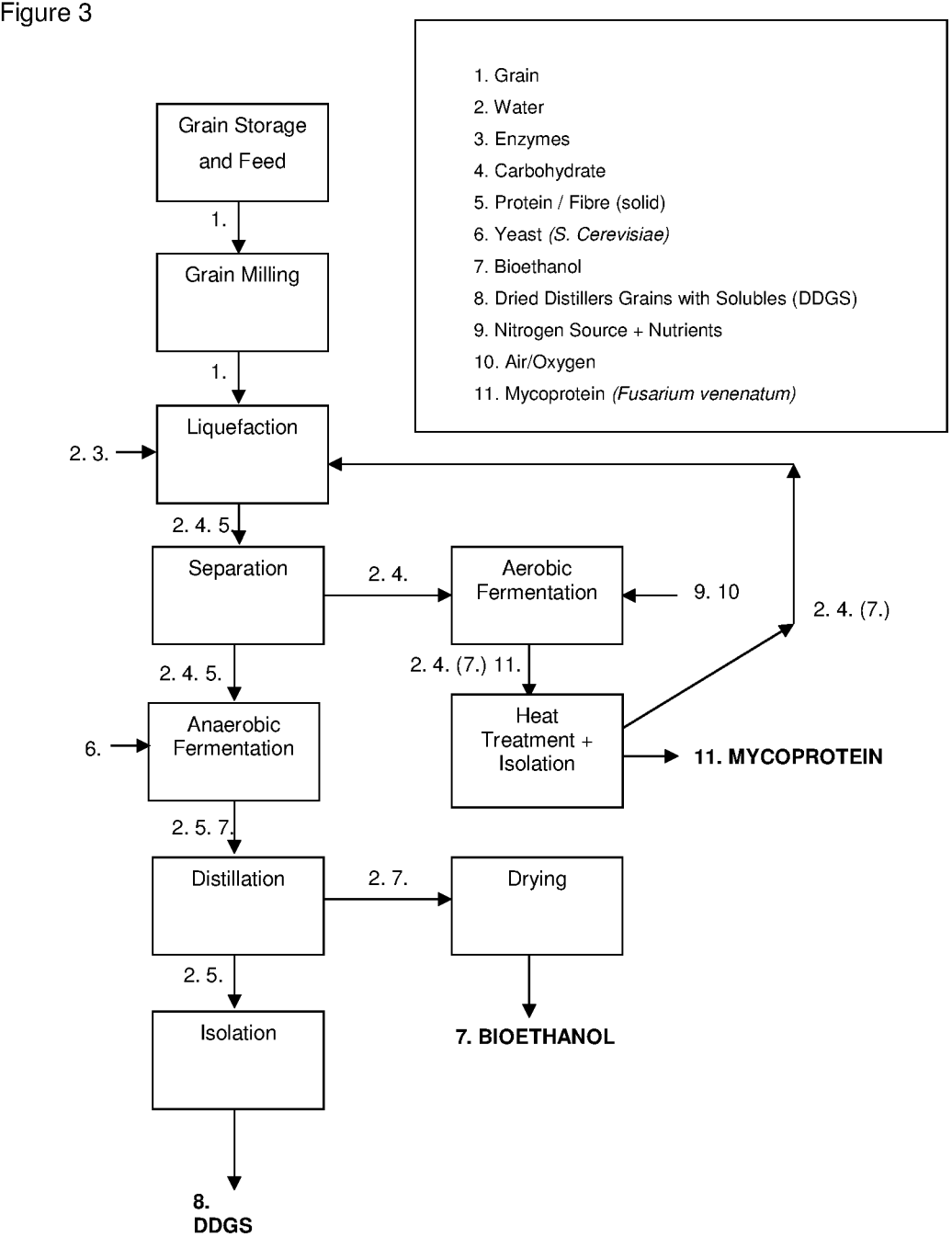

FIG. 3 Further flow diagram of an integrated configuration of co-production method for mycoprotein and ethanol production using two microorganisms.

Figure 4:
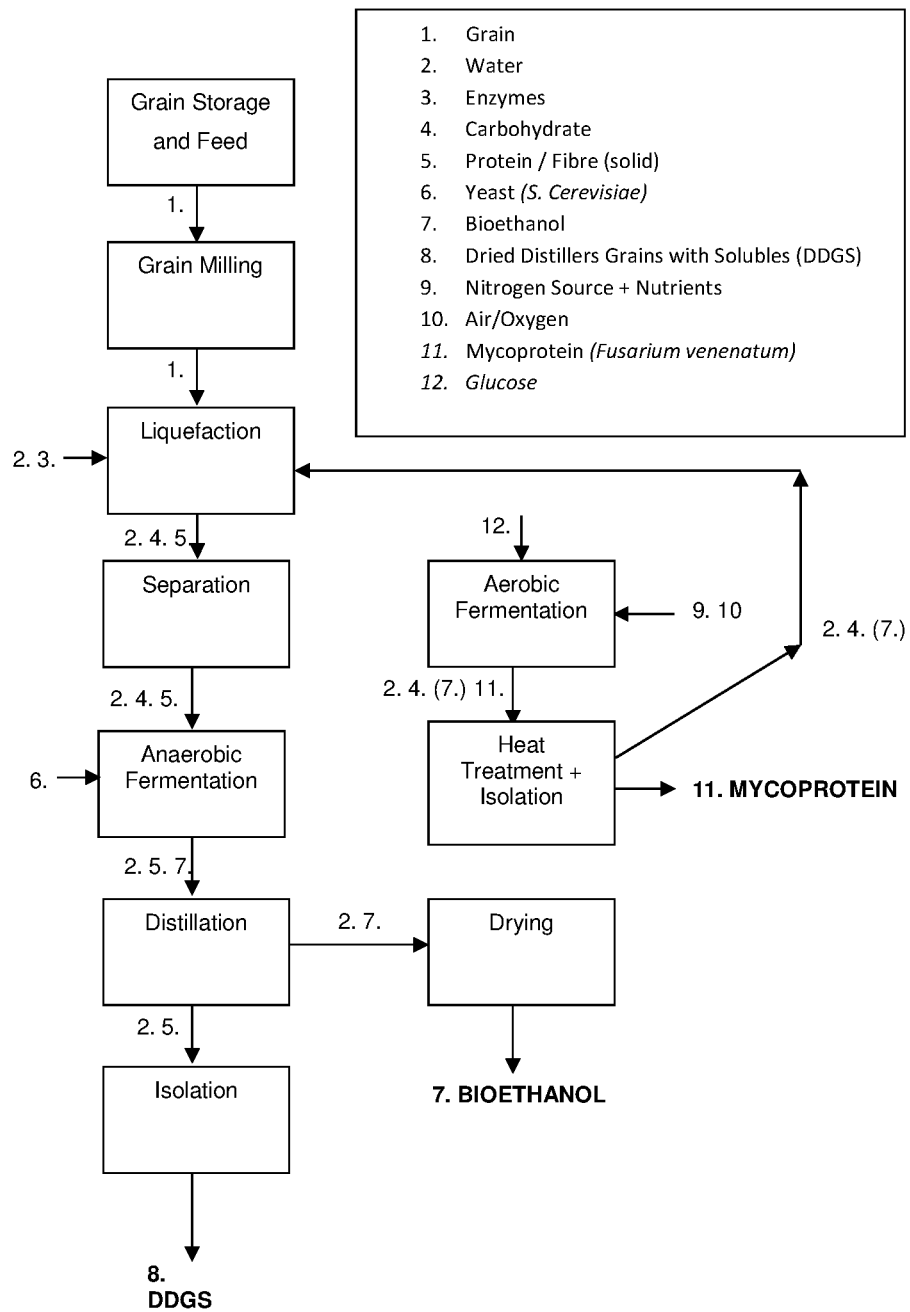

FIG. 4 Further flow diagram of an integrated configuration of co-production method for mycoprotein and ethanol production using two microorganisms and different feedstocks.

Figure 5:
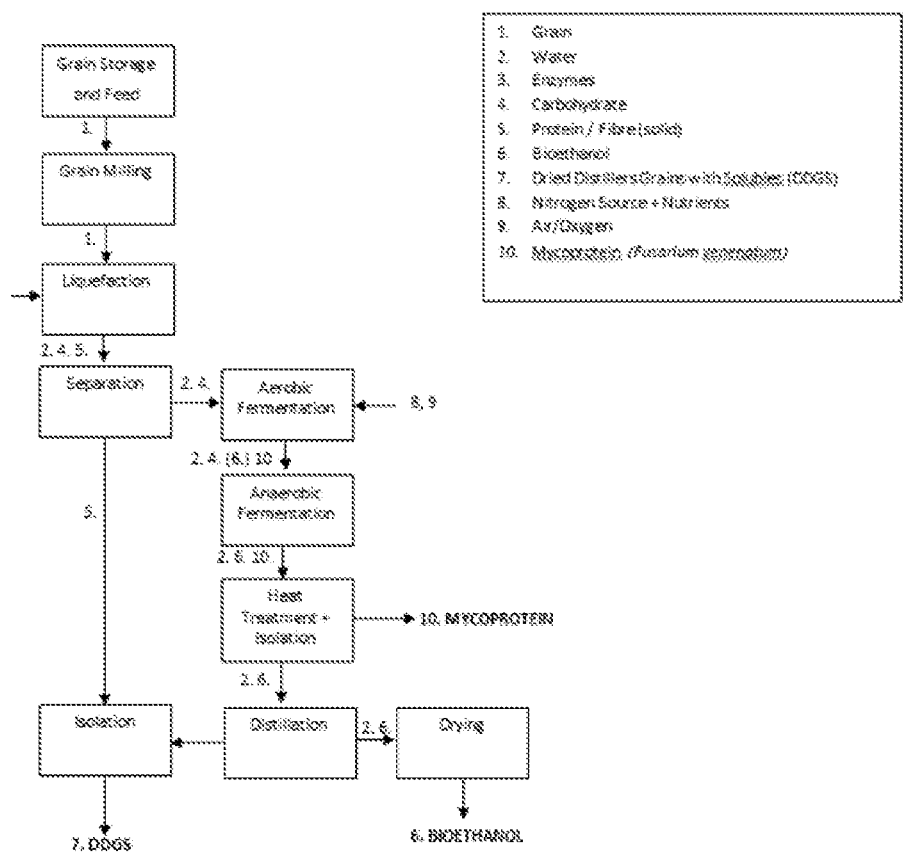

FIG. 5—Flow diagram of a possible integrated configuration of co-production method for mycoprotein and ethanol production using a single microorganism (Aerobic fermentation followed by anaerobic fermentation).

Figure 6:
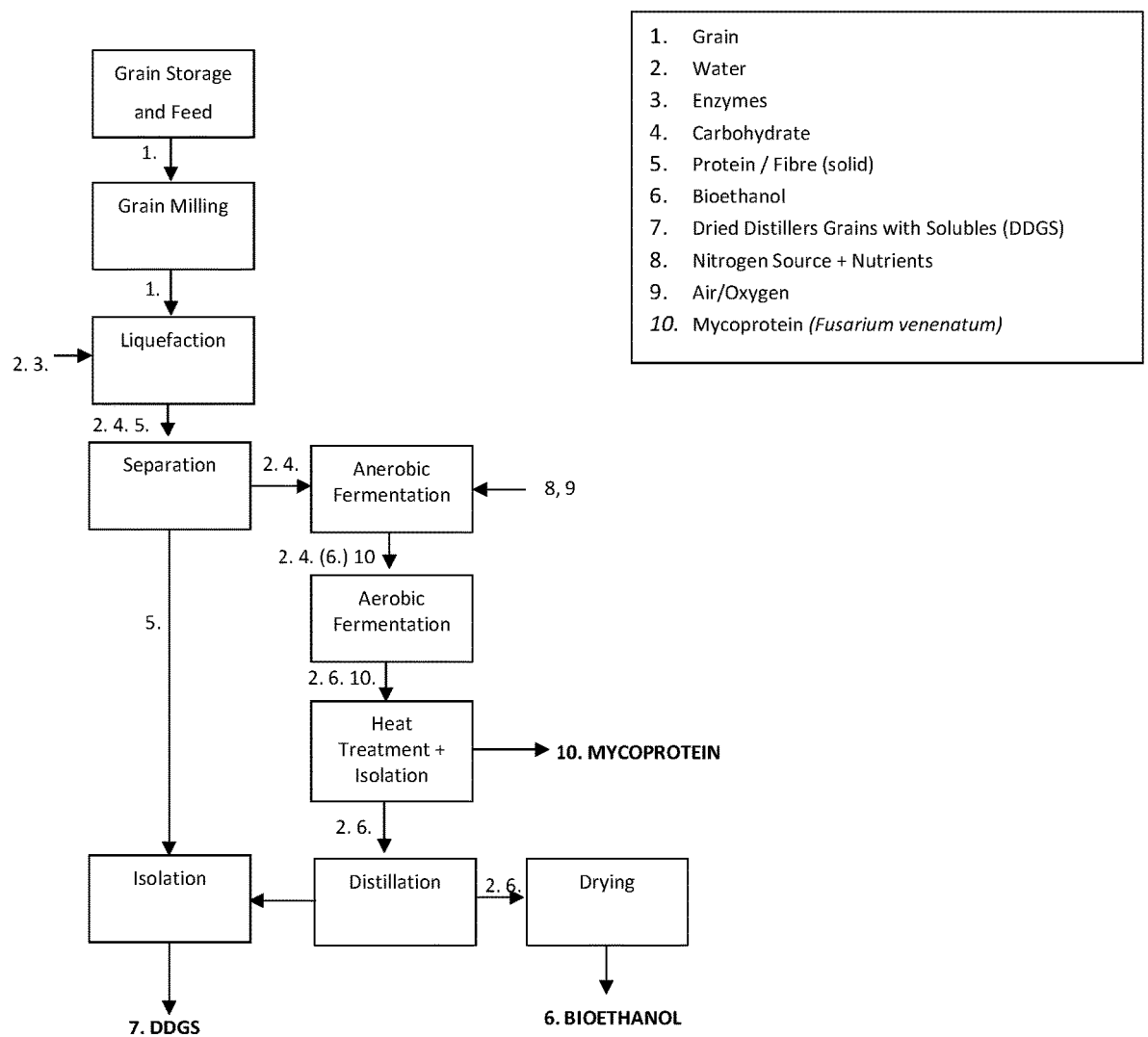

FIG. 6—Flow diagram of an integrated configuration of co-production method for mycoprotein and ethanol production using a single microorganism (Anaerobic fermentation followed by aerobic fermentation).

Figure 7:
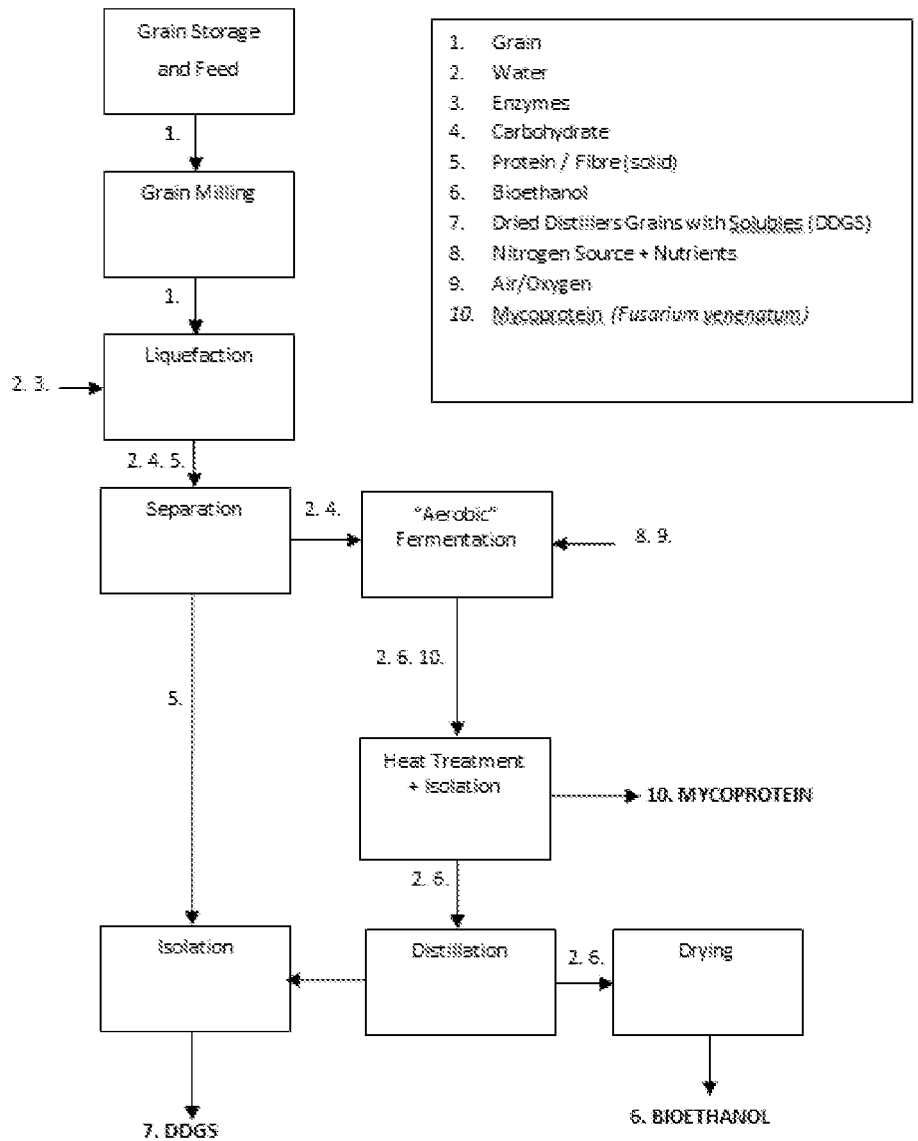

FIG. 7—Flow diagram of an integrated configuration of co-production method for mycoprotein and ethanol production using a single microorganism.

Figure 8:
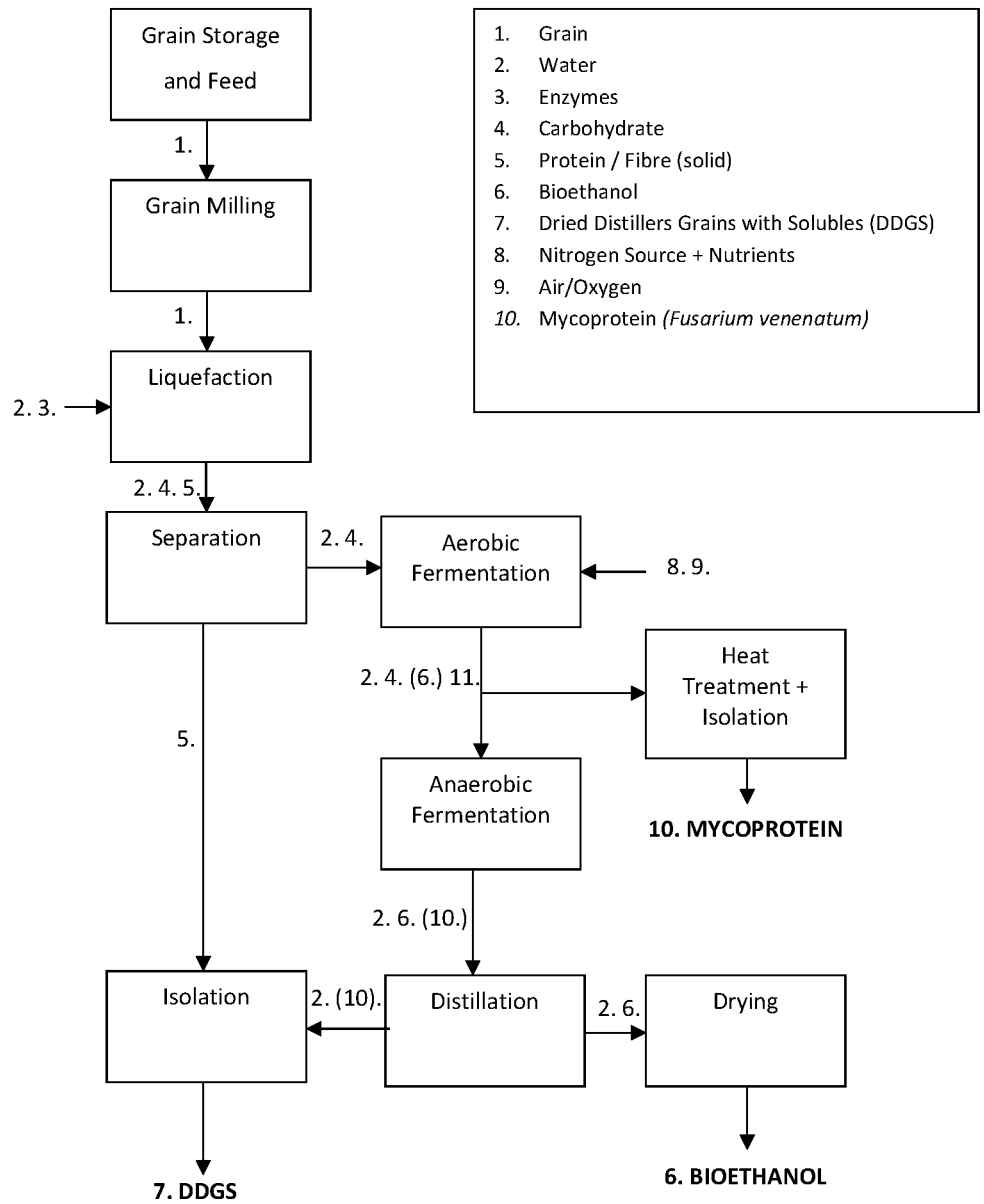

FIG. 8—Flow diagram of an integrated configuration of co-production method for mycoprotein and ethanol production using a single microorganism (Anaerobic fermentation followed by aerobic fermentation).

Figure 9:
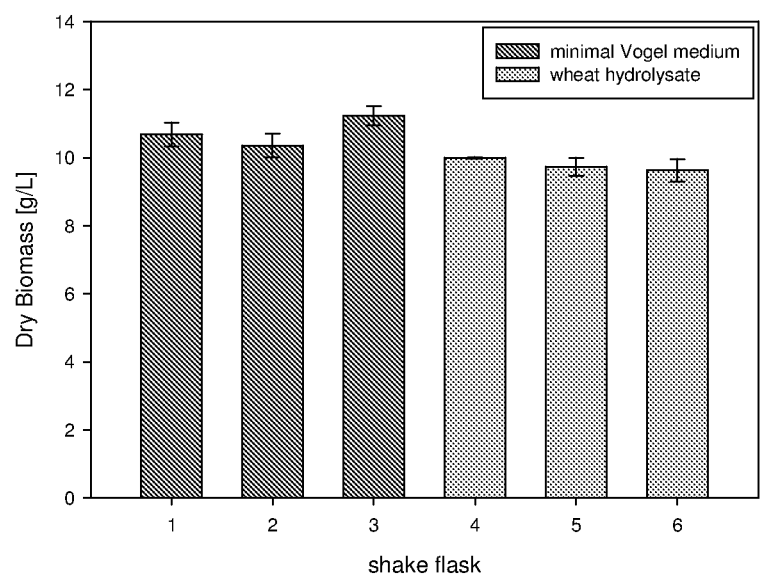

FIG. 9—Comparison of growth of *F. venenatum* in minimal Vogel medium (flasks 1-3) and wheat hydrolysate supplemented with Vogel salts (flasks 4-6). The shake flasks were incubated on an orbital shaker at 30° C. and 150 rpm. The experiment was performed in triplicate as well as the estimation of the biomass. Samples were taken after 72 h (Experiment 1).

Figure 10:
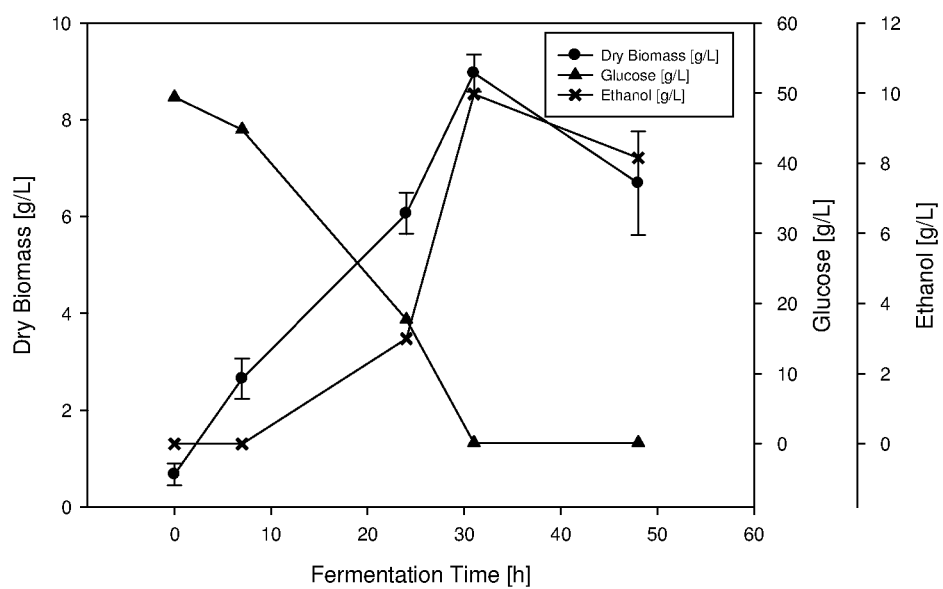

FIG. 10—Batch fermentation of *F. venenatum* (Vw=1.5-L) with wheat hydrolysate supplemented with Vogel salts. Shown is the dry biomass (●), glucose (▲) and ethanol (x) trend over the course of the fermentation (Experiment 1).

Figure 11:
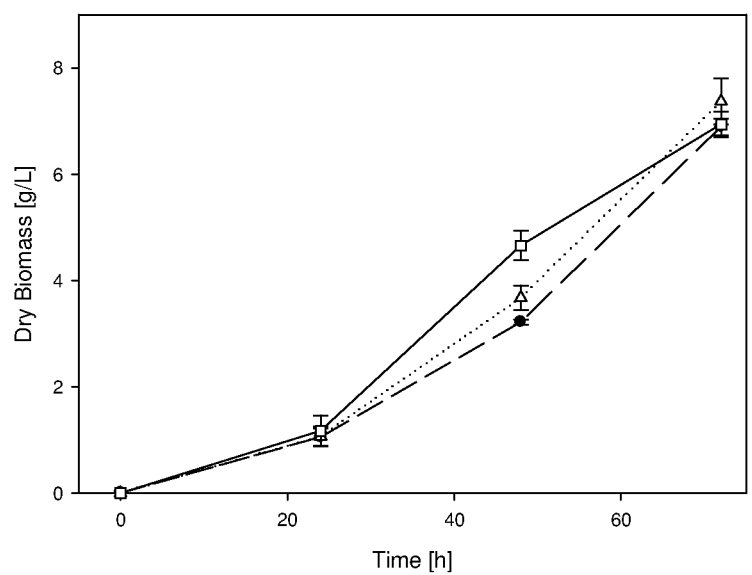

FIG. 11—Growth of *F. venenatum* in 70 g/L flour containing hydrolysate without enzymes (●), with 0.5% w/w α-amylase (Δ) and with both 0.5% w/w α-amylase and 1% w/w glucoamylase (□) grown in shake flasks at 28° C. and 150 rpm on an orbital shaker. Samples were taken after 24, 48 and 72 hours and analysed in triplicate for biomass content (Experiment 1).

Figure 12:
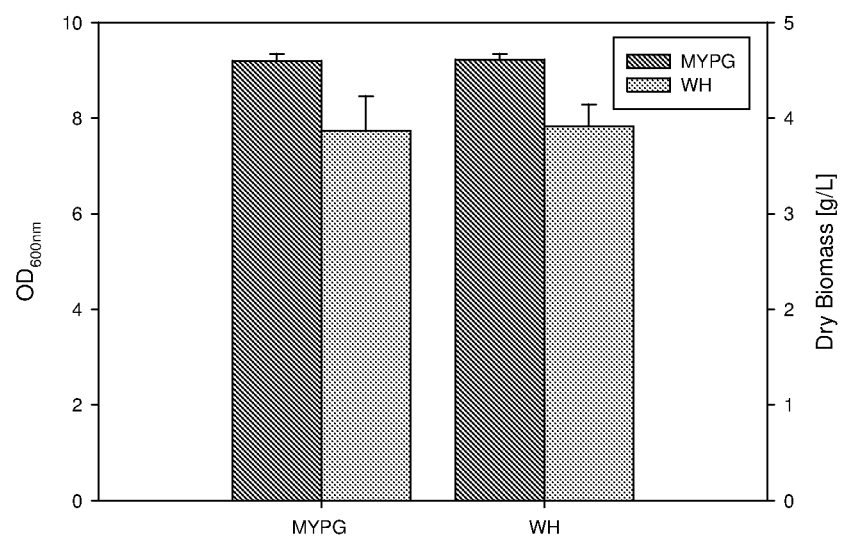

FIG. 12—Optical density (OD) and Dry Cell weight of *S. cerevisiae* shake flasks with MYPG and wheat hydrolysate supplemented with Vogel salts. The flasks were incubated at 30° C. and 250 rpm and all contained 20 g/L glucose as a carbon source. They were grown and analysed in triplicate (Experiment 2).

Figure 13:
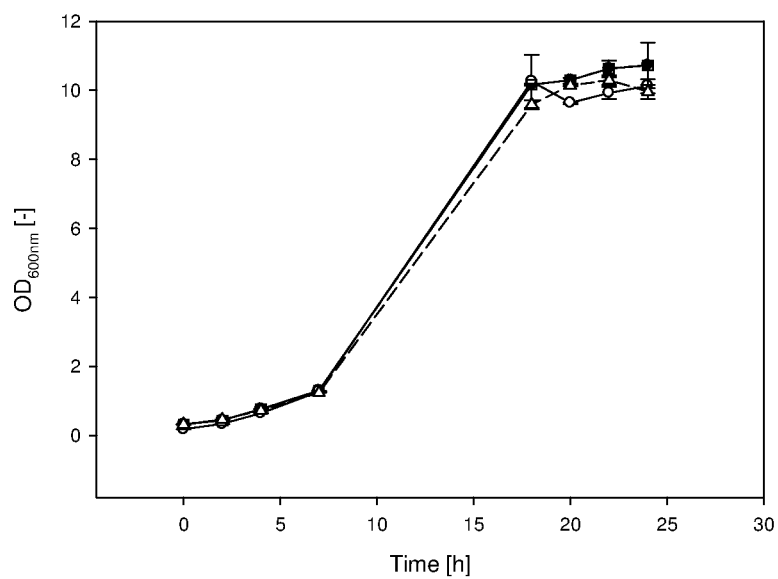

FIG. 13—Ethanol fermentation with *S. cerevisiae* using MYPG and Wheat Hydrolysate respectively. Depicted are the optical densities over the course of the fermentation. MYPG was used in fermenter 1 (●) and fermenter 2 (○) whereas wheat hydrolysate supplemented with Vogel salts was used in fermenter 3 (□) and fermenter 4 (Δ). Aeration was 0.82 vvm between 8-18 h otherwise 0 vvm. The temperature was held constant at 30° C. and the pH at 5.5 (Experiment 2).

Figure 14:
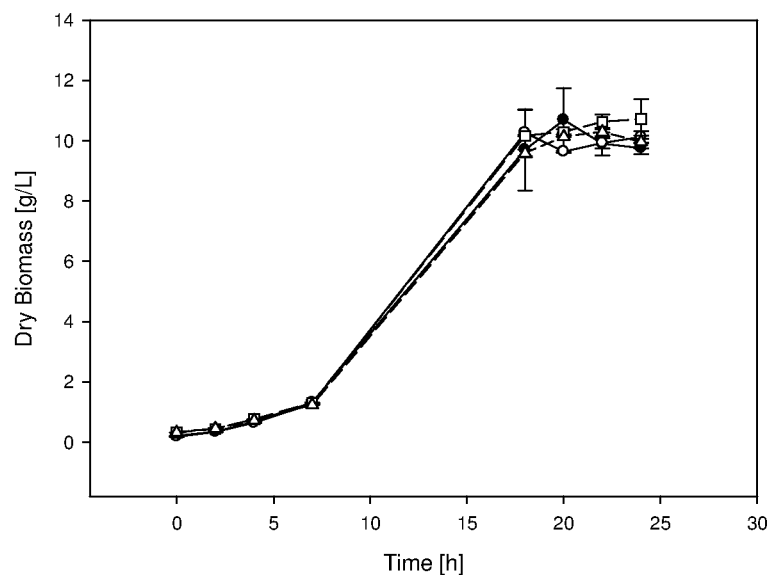

FIG. 14—Ethanol fermentation with *S. cerevisiae* using MYPG and wheat hydrolysate respectively. Shown is the dry biomass increase over the course of the fermentation. MYPG was used in fermenter 1 (●) and fermenter 2 (○) whereas wheat hydrolysate supplemented with Vogel salts was used in fermenter 3 (□) and fermenter 4 (Δ). Aeration was 0.82 vvm between 8-18 h otherwise 0 vvm. The temperature was held constant at 30° C. and the pH at 5.5 (Experiment 2).

Figure 15:
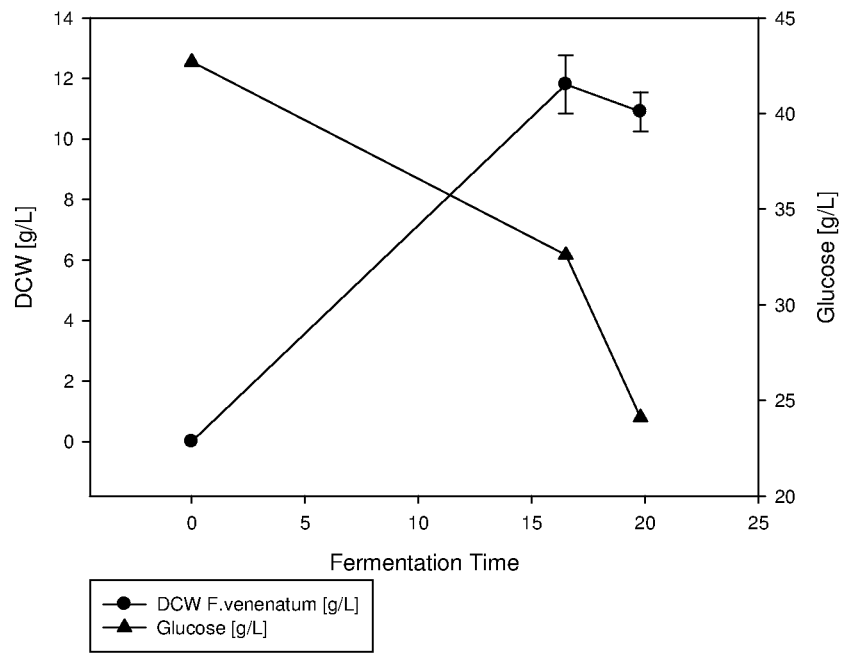

FIG. 15—Dry cell weight (DCW) and glucose trend for first fermentation of the integrated process with *F. venenatum* (Experiment 3).

Figure 16:
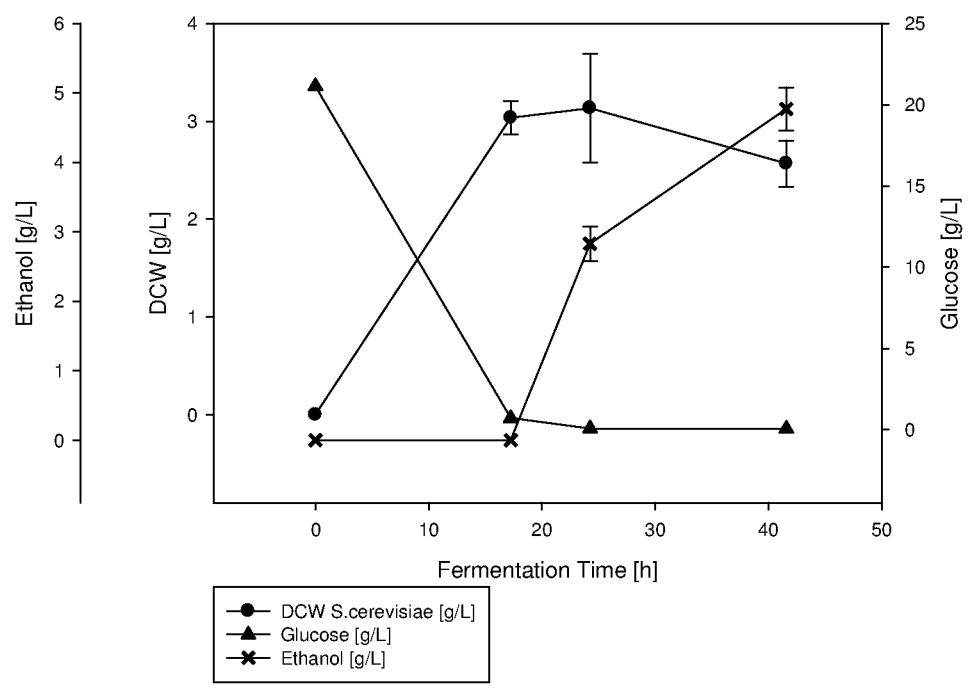

FIG. 16—Dry cell weight (DCW), glucose and ethanol trends for second part of integrated bioprocess with *S. cerevisiae*

Figure 17:
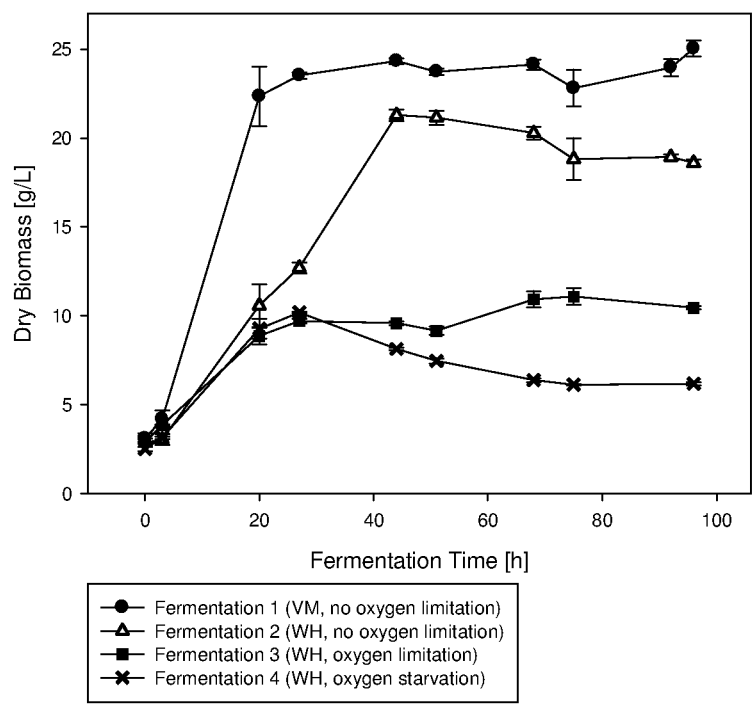

FIG. 17—Comparison of the dry cell weight trends of the *Fusarium venenatum* fermentations with the application of different aeration profiles (Experiment 4).

Figure 18:
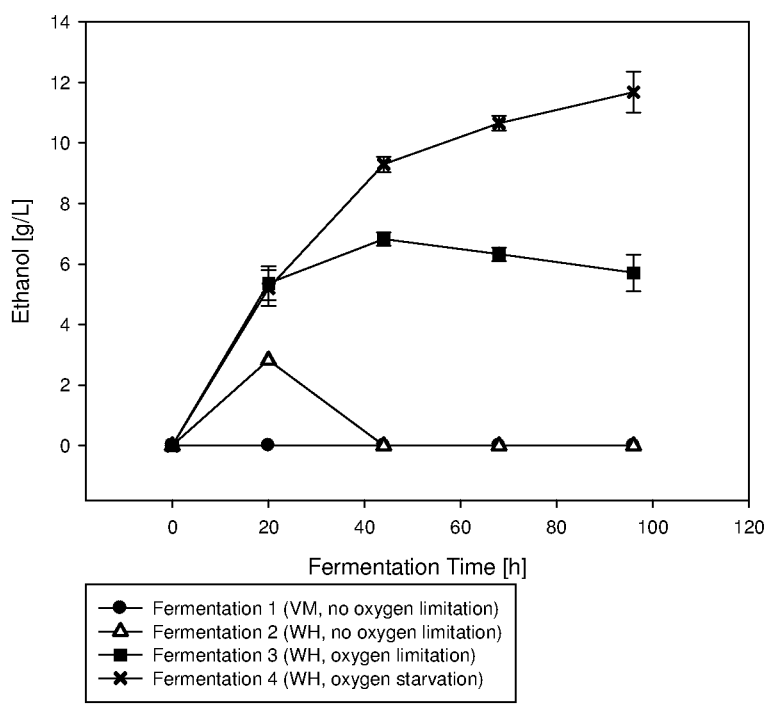

FIG. 18—Ethanol production over the course of the *Fusarium venenatum* fermentations with varying oxygen supply (Experiment 4).

Figure 19:
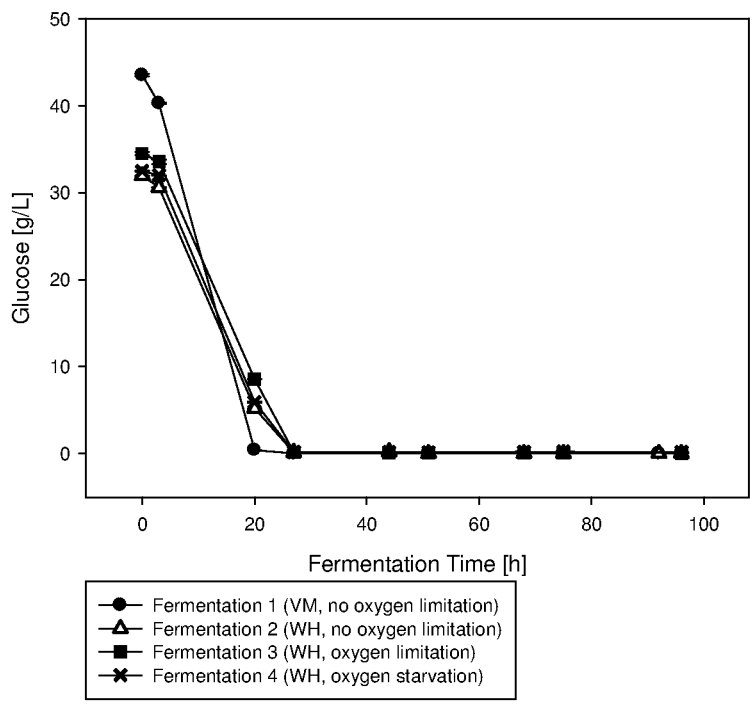

FIG. 19—Trend of glucose concentrations over the course of the *F. venenatum* fermentations with different fermentation media and differing oxygen supply (Experiment 4).

Figure 20:
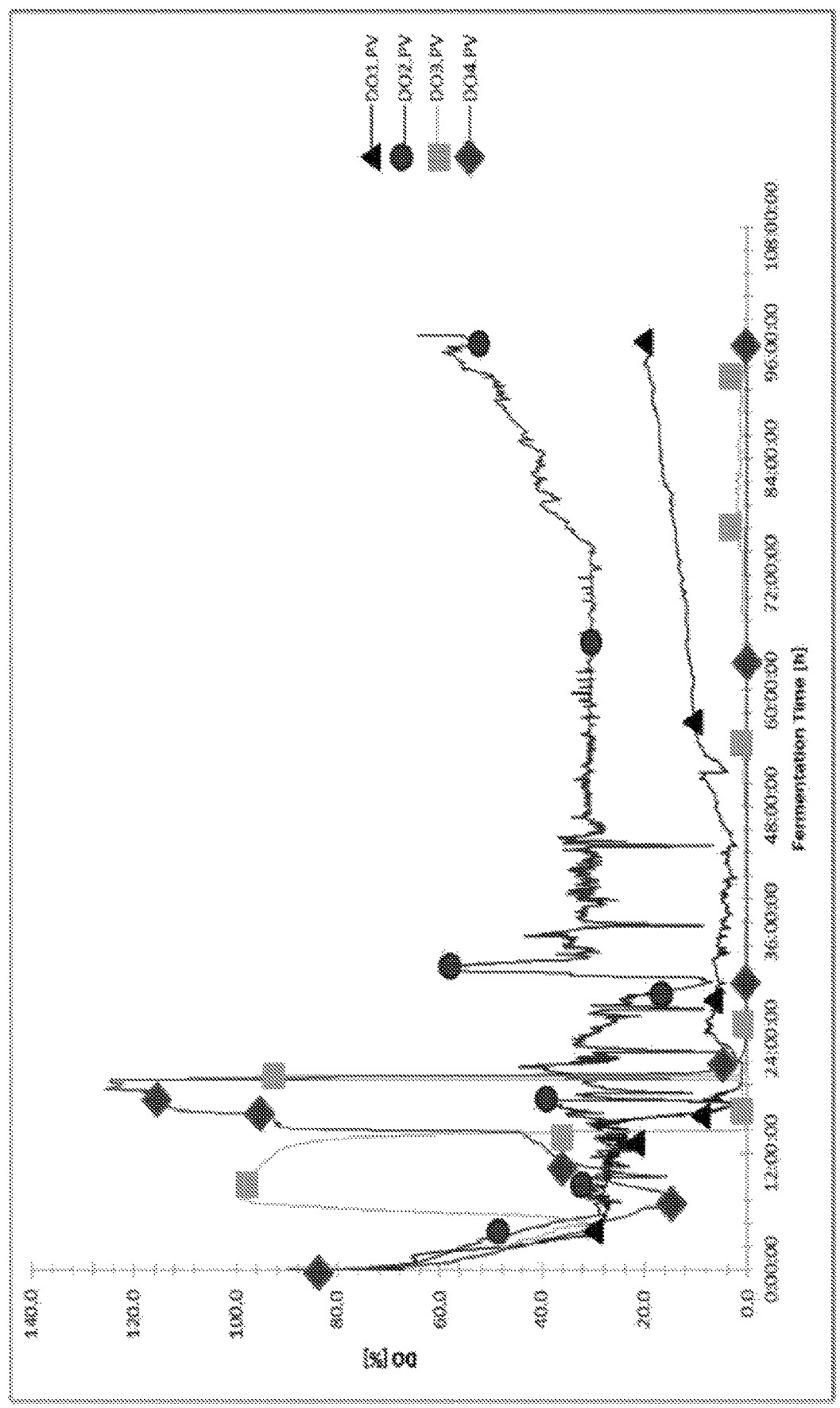

FIG. 20—Dissolved oxygen (DO, %) profile during the time course of *F. venenatum* fermentations (Experiment 4).

The following key is to be used in order to interpret the various components and steps which are carried out in the processes exemplified in FIGS. 1-8:

Grain milling physically breaks down the grain to enable starch extraction in downstream processing;

Liquefaction is a process to extract and hydrolyse the starch from the grain to obtain water soluble carbohydrates suitable for physical processing and fermentation. The grain is mixed and heated with water, typically with the use of enzymes. The heating process additionally sterilises the solution for fermentation;

Separation of the solid protein and fibre by decantation, filtration or centrifugation is carried out to provide a soluble carbohydrate solution suitable for mycoprotein fermentation. This step is not necessary in conventional ethanol bio-refining since the fermentation product ethanol can be distilled from the slurry;

Aerobic Fermentation provides fermentation growth of the mycoprotein. This operation can be carried out in either batch or continuous mode. A nitrogen source (eg ammonia), nutrients and air/oxygen are fed to the fermenter with cooling under controlled conditions to favour mycoprotein growth. Conditions can be controlled to optimise mycoprotein growth rate/selectivity or to achieve a preferred ratio of mycoprotein to ethanol by manipulating physiological conditions through process variables such as substrate flux or/and oxygen level;

Heat Treatment and Isolation of the mycoprotein fermentation brew provides an isolated (by filtration or centrifugation) and dried solid bulk mycoprotein product. The heat treatment of the mixture is carried out to reduce the nucleic acid (RNA) content of the product;

Anaerobic Fermentation is carried out to convert residual carbohydrates to ethanol. This can be carried out using either or both mycoprotein and conventional brewer's yeast (e.g. *S. cerevisiae*);

Distillation is used to separate ethanol from the fermentation mixtures;

Drying removes residual water from the distilled ethanol to satisfy the specification of bio-ethanol fuel. This is conventionally carried out using molecular sieves; Isolation of the solid protein/fibre from the grain produces a high protein product typically used as livestock feed. When isolated and dried together with the evaporated residue from distillation incorporating the soluble components of the fermentation mixtures it is conventionally called distillers dried grains with solubles (DDGS).

shows a representative process known in the art for preparing bioethanol alone. In this process only an anaerobic process is described for the production of the bioethanol.

As can be seen from the various processes exemplified in -8 the present invention provides a separation phase where insoluble materials such as protein and fibre are removed in order to provide a solution which comprises solubilised carbohydrates suitable for subsequent fermentation.

In the various embodiments depicted in FIGS. 2-8 an integrated process is provided which can produce both ethanol and mycoprotein, as well as a spent waste material, dried distiller grains with solubles (DDGS) which may be used as an animal feed product.

EXAMPLES SECTION

Experimental Procedures 1.1 Microorganisms and Culture Conditions

The microorganism used in the mycoprotein (and ethanol) fermentations was the filamentous fungus *F. venenatum* A3/5 (20334), purchase from ATCC. Master cultures were produced by inoculating liquid cultures containing minimal Vogel medium with 40 g/L glucose from potato dextrose agar (PDA) plates. They were incubated for 72 h at 150 rpm and 28° C. on an orbital shaker, before adding 20% glycerol to the cultures and storing them at −80° C. in cryo vials. Furthermore PDA plates were grown at 30° C. and 0% $CO_2$ in an incubator and then stored at 4° C.

For the ethanol fermentation the yeast *S. cerevisiae* was also used (supplied from the culture collection of Strathclyde Institute of Pharmacy and Biomedical Sciences). It was grown in MYPG medium with 1 L containing: 3 g malt extract, 3 g yeast extract, 5 g peptone and 10 g glucose, whereas the glucose was added after autoclaving in order to prevent the Maillard reaction. The pH was adjusted to 5.5 and to solidify the medium 15 g/L agar were added. Plates were inoculated with a loop and incubated for 24 h at 30° C. in an incubator and then stored at 4° C. Master cultures were produced by inoculating a liquid culture and incubating it for 24 h on an orbital shaker at 30° C. and 250 rpm prior to adding 20% glycerol and storing at −80° C. in cryo vials.

1.2 Inoculum Preparation

The inoculum of *F. venenatum* was prepared by inoculating a de-frosted vial from the −80° C. cell bank into a 200 mL aliquot of Vogels media. The culture was incubated at 30 degree's for a period of twenty-four hours. A 50 mL aliquot of this culture (giving an inoculum of 10% v/v) was removed and transferred to a centrifuge tube. This was centrifuged at 8000 rpm for a period of 10 minutes. The supernatant was removed and an equal volume of sterile distilled water was added to re-suspend the pellet of *F. venenatum*. This was then centrifuged as before at 8000 rpm for a 10 minute period. The supernatant was again removed and the *Fusarium* venentum pellet re-suspended in a 20 mL aliquot of sterile wheat medium. This aliquot was used to inoculate the bioreactor via the syringe septum port.

Preparation of the *S. cerevisiae* inoculum followed a similar approach. A vial from the cell bank was defrosted and used to inoculate a 200 mL flask containing MYPG media. When the cell density had reached sufficient levels (optical density of approximately 1 Au) a 50 mL aliquot of the culture was centrifuged, washed with distilled water, and re-suspended in wheat media following the same procedure as was carried out with the *F. venenatum* inoculum.

1.3 Medium Preparation 1.3.1 Defined Medium

The defined medium used for the fermentation and shake flasks was prepared according to Vogel (1956). The carbon source sucrose was substituted with glucose and 40 g/L instead of 15 g/L were used.

1 L of medium contained: 2.17 g Trisodium citrate, 5 g Potassium dihydrogen phosphate, 2 g Ammonium nitrate, 0.2 g Magnesium sulfate heptahydrate, 0.1 g calcium chloride dihydrate, 0.25 mg Biotin and 5 mL Trace Element Solution.

For the trace element solution the following trace elements were dissolved in 95 mL distilled water: 5 g Citric acid monohydrate, 5 g zinc sulfate heptahydrate, 1 g ammonium ferrous sulphate hexahydrate, 0.25 g cupric sulfate pentahydrate, 0.05 g manganese sulfate monohydrate, 0.05 g boric acid and 0.05 g sodium molybdate dihydrate.

1.3.2 Wheat Hydrosylate (WH)

The wheat grain was milled to a flour material using an IKA analytical mill. This flour was dissolved in distilled water heated to 90° C. with a final flour concentration in the region of 70 g/L. Once in solution the pH of the system was adjusted to 7 before the addition of α-amylase enzyme at a loading of 1% w/w of the added wheat flour. This solution was maintained at 90° C. and agitated for a 1 hour period. The solution was then allowed to cool whilst still being agitated until a temperature in the region of 50° C. was reached. The pH of the solution was then adjusted to 4.6-4.8 using 1 M hydrochloric acid. The glucoamylase enzyme was then added again with a loading of 1% w/w relative to the amount of wheat flour added. This solution was then incubated for a 16 hour period in a shaking incubator at 50° C. and 100 rpm.

The enzyme treated media was then cooled to room temperature, transferred to centrifuge vessels and centrifuged at 6,000 rpm for a 10-minute period. The supernatant was passed through a 0.2 μm filter paper using a Buchner funnel and the filtrate collected for use in the fermentation process. The filtrate was then autoclaved again. The procedure of the starch hydrolysis was performed referring to Panagiotopoulos et al. (2009), Gadonna-Widehem et al. (2012) and the enzyme datasheets provided by Sigma.

1.4 Biomass Estimation

The biomass levels of *F. venenatum* and *S. cerevisiae* were estimated for each of the samples taken during the fermentations.

*F. venenatum* cell weight estimation was achieved using microfiber filters. A glass microfiber filter was numbered and the mass of the dry filter recorded. The filter was placed in a Buchner funnel and a 1 mL aliquot of the fermentation sample passed through the filter. This process was repeated in triplicate for each sample. Filters were subsequently placed in a petri dish and dried in an oven at 50° C. for a period of 24 hours. The filters were then re-weighed, and if necessary dried again until a stable reading was observed. Biomass was calculated by subtracting the previously recorded weight of the empty filter. Since the process was carried out in triplicate the reported value was the average of the three weights recorded.

*S. cerevisiae* dry cell weight estimation was carried out using eppendorf tubes. Eppendorf tubes were dried in a desiccator and the weight of the dry, empty tube recorded. A 1 mL aliquot of the fermentation sample was pipetted into the tube and then centrifuged at 6000 rpm for a 10-minute period. The supernatant was removed and the cell pellet dried. The tube was re-weighed, until a stable reading was observed, and the mass of the empty tube subtracted to give the mass of cells present. Since a 1 mL aliquot of the fermentation sample was utilised, the value determined here was quoted as the dry cell weight in g/mL. All samples were again analysed in triplicate with the quoted value the average of the three replicates.

1.5 Glucose Quantification

The glucose concentration present in each sample was measured using the YSI biochemistry analyser. Early samples required a dilution factor in the region of ×10 to be applied in order to reduce the glucose concentrations to levels that the biochemistry analyser was able to reproducibly quantify. During the *Saccharomyces* fermentation the later samples could be analysed directly without the need for any dilution steps to be performed.

1.6 Ethanol Quantification

The quantification of ethanol in the samples was achieved using a high performance liquid chromatography (HPLC) method. Separation was achieved using a REZEX ROA-$H^+$ organic acid chromatography column and a 0.005 N sulphuric acid mobile phase at a flow rate of 1 mL/min. Detection was via a refractive index detector.

1.7 Shake Flask Cultivation

Shake flask culture cultivations were performed in 500 mL or 100 mL conical flasks containing 200 mL or 40 mL medium (MYPG or Wheat Hydrolysate with Vogel salts). The flasks were incubated on a vertical shaker set to 150 rpm and 28° C. for *F. venenatum* cultures and at 30° C. and 250 rpm for *S. cerevisae* cultures.

1.8 Bioreactor Batch Cultivation 1.8.1 *F. venenatum* Batch Cultivation

The mycoprotein batch fermentations were performed in two different fermentation systems which are described below. The fermentation temperature was 28° C. and the pH was controlled to 6 with 2M sodium hydroxide. The DO probe was calibrated with oxygen free nitrogen for the 0% $O_2$ value and the slope calibration was performed with compressed air. The probe calibration was performed at fermentation conditions. The inoculum, a 72 hour shake flask culture grown at 28° C. and 150 rpm on a vertical shaker, made up 10% v/v of the final fermentation volume. The medium used for the fermentation was either Medium N (Vogel 1956) or wheat hydrolysate supplemented with Vogel salts. In case of using the wheat hydrolysate as the fermentation medium, rapeseed oil was used as an antifoam reagent whenever required.

1.8.1.1 Applikon

The borosilicate vessel of this fermentation system has a total volume of 2 L and the fermentations were performed at a working volume of 1.5 L with a height to diameter ratio of 2:1. The fermenter is equipped with four removable baffles and two six bladed Rushton impellers, powered by an overhead Applikon P100 Motor. The aeration was realised by sparging filtered air through a ring sparger positioned underneath the impeller. The pH was measured with a Mettler Toledo pH probe and for determination of the dissolved oxygen a Mettler Toledo DO probe was used. An Applikon heating jacket was used to heat the fermenter. The system was furthermore equipped with a temperature probe and a condenser to prevent evaporation. An Applikon Bio-Console ADI 1035 unit was used in combination with the Applikon Bio-Control ADI 1031 control unit to control the parameters. The agitation used with this fermentation system was 600 rpm.

1.8.2 Ethanol fermentation

The ethanol fermentation was performed in two different fermentation systems described below in detail. The agitation used was 500 rpm and the temperature was controlled at 30° C. The $pO_2$ probe calibration was performed at fermentation conditions. The 0% O2 value was set by aerating with oxygen free nitrogen and the slope of the probe was calibrated with compressed air. The pH was controlled with 2M sulphuric acid and 25% v/v ammonia to a value of 5.5. The fermentation broth was only aerated with 0.82 vvm between 8 and 18 hours of fermentation time. The inoculum, a 24 hour shake flask culture (30° C., 250 rpm), made up 5% v/v of the final fermentation volume. To control foaming during the fermentation PPG was added as required.

1.8.2.1 Biostat C (C15-3) with DCU 3 (B.Braun Biotech)

The stainless steel fermenter has a total volume of 22 L and a double wall which allows heating or cooling of the fermenter. It was a side wall viewing window and is equipped with four baffles, as well as three six bladed Rushton impellers which are above a ring sparger. The $pO_2$ probe as well as pH probe were from Mettler Toledo. The height to diameter ratio was 3:1 with a diameter of 21 cm and a height of 57 cm. The DCU-3 Unit allowed controlling and monitoring of the fermentation. The pH was controlled with help of the acid and base pumps. Furthermore the system is equipped with an antifoam pump which was used as required.

1.8.2.2 DASGIP (Eppendorf)

The fermentation system allows the performance of four parallel fermentations, which can be controlled independently. The flat bottom fermenter vessels have a diameter of 9 cm and a height of 24 cm which equals a height to diameter ratio of 3:1. The vessels have a working volume of 400-1500 mL. The overhead drive agitates the two six bladed Rushton impellers. Aeration is achieved by pumping air through a sterile filter through an L-sparger. The system is fully equipped with a main unit which heats the vessels, acid and base pumps, pH and $pO_2$ detection units, temperature detector, off-gas analysis, and agitation control.

Results 1.9 Wheat Media

The wheat media utilised for this fermentation was obtained following the procedure outlined (1.3). This particular media preparation was using the 'RCS' identified batch of wheat with a loading of 146 g wheat flour dissolved in 2 L of distilled water. An enzyme loading of 1.46 g of α-amylase and 1.5 g of glucoamylase were utilised in the process.

Glucose concentrations measured using the YSI biochemical analyser at the various stages in the media preparation, are listed in Table 1.

TABLE 1

Glucose concentrations at various stages during enzyme treatment of wheat media.

| Stage | Glucose 1 (g/L) | Glucose 2 (g/L) | Glucose 3 (g/L) | Dilution Factor | Mean Glucose (g/L) |
|---|---|---|---|---|---|
| Pre-enzyme addition | 0.045 | 0.046 | 0.047 | None | 0.046 |
| Post α-amylase | 0.588 | 0.589 | 0.583 | None | 0.587 |
| Pre glucoamylase addition | 0.653 | 0.639 | 0.651 | None | 0.648 |
| Post Filtration | 4.65 | 4.53 | 4.38 | x10 | 45.20 |

The following experiments were performed to support the invention.

TABLE 2

Experiments supporting the invention.

| Experiment | Aim |
|---|---|
| Experiment 1 | Production of mycoprotein from a carbohydrate feedstock (wheat hydrolysate) using a single microorganism. |
| Experiment 2 | Production of ethanol from a carbohydrate feedstock (wheat hydrolysate) using a single microorganism. |
| Experiment 3 | Production of mycoprotein and ethanol by a 2 step fermentation with partial conversion of the carbohydrate in the first step and where the operating conditions are controlled in favour of each product. Two microorganisms are used. |
| Experiment 4 | Production of mycoprotein and ethanol by a 2 step fermentation with partial conversion of a carbohydrate feedstock (wheat hydrolysate) in the first step and where the operating conditions are controlled in favour of each product (no oxygen limitation, oxygen limitation and oxygen starvation). A single microorganism is used. |

1.10 Experiment 1

1.10.1 Aims & Objectives

The objective of this experiment was to investigate the feasibility of growing F. venenatum for mycoprotein production using a carbohydrate feedstock (wheat hydrolysate).

1.10.2 Experimental Conditions

Shake flask cultures of F. venenatum were initially grown in wheat hydrolysate and in glucose (both media supplemented with Vogel salts) to compare the growth profile in the two different medium. Flasks were performed and analysed in triplicate. Samples were taken after 72 hours and analysed for biomass and glucose content (9).

The fermentation set-up for the mycoprotein fermentation was: aeration with 1 slpm and the stirrer speed was set to 1000 rpm. The temperature was held at 28° C., the pH was set to 6 and the fermenter was inoculated with a 72 h shake flask culture of 10% v/v of the final fermentation volume. The wheat hydrolysate for the fermentation was supplemented with Vogel salts. The first fermentations revealed the problem of strong build-up of foam at the beginning of the fermentation. This led to accumulation of biomass in the foam and in conclusion only growth on top of the fermentation broth but not in solution. The foaming is presumably caused by the proteins in the wheat hydrolysate and as the minimal Vogel medium used in previous fermentations did not contain proteins foaming was not an issue in previous batch fermentations and furthermore also does not present a problem in the current used industrial process.

To overcome this problem rapeseed oil was used as an antifoam reagent. Rapeseed oil was chosen because it could be used in a food grade product and would be an economical solution. It may also be used as a carbon source by the *Fusarium* which would lead to higher yields and as foaming was only a significant problem at the beginning of a process this would not be a problem at later time points.

As the use of rapeseed oil as an antifoam reagent alone could not overcome the problem of accumulation of the inoculum on top of the liquid level in the fermenter, an aeration and agitation profile was used. In detail this means that the agitation and aeration were slowly raised over a time course of 1.5 hours. The used agitation and aeration rates are shown in the table below.

TABLE 3

Agitation and aeration profile of the batch fermentation of *F. venenatum* with wheat hydrolysate. Depicted are the time points when the parameters were raised.

| Fermentation time [h] | Agitation [rpm] | Aeration [L/min] |
| --- | --- | --- |
| 0 | 150 | 250 |
| 0.5 | 300 | 500 |
| 1 | 450 | 750 |
| 1.5 | 600 | 1000 |

1.10.3 Results

With the use of this profile a successful batch fermentation was performed which can be seen in 10. The maximal reached biomass in this fermentation was 8.97 g/L which taking into account a starting glucose concentration of 49.46 g/L gives a yield of 18.1%. This reached yield is only half of the yield which was reached in the batch fermentation with minimal Vogel medium. This is probably due to a strong oxygen limitation at the beginning of the fermentation which crucially restricts growth. The dissolved oxygen decreases rapidly at the beginning of the fermentation as the aeration and agitation is very low at the beginning which is disadvantageous for oxygen transfer into the fermentation broth (data not shown). A higher mycoprotein yield could possibly be reached by improving the oxygen supply, as also 9.98 g/L ethanol was produced as a side product during the fermentation. The production of such high levels of ethanol during this fermentation were not expected and further experiments will be done to investigate the effect of culture conditions on the co-production of ethanol and mycoprotein by *F. venenatum* (section 1.13).

1.10.3.1 *F. venenatum* Growth in Partially Hydrolysed Media (No Use of Enzymes)

Due to considerations about the economy of the process and the high costs in the purchase of hydrolysing enzymes and the high costs of the hydrolysing process due to heating/cooling steps and pH adaptations, it was taken into account to use wheat flour which was only dissolved in water or partially hydrolysed wheat by only performing the liquefaction step. To investigate what influence this would have on the growth of the *Fusarium* strain, *Fusarium* it was grown in shake flasks in different hydrolysates supplemented with Vogel salts. For this purpose 70 g/L wheat flour were dissolved in 90° C. water and then only the liquefaction step was performed with 0.5% w/w α-amylase in one sample and both the liquefaction and saccharification step with the additional use of 1% w/w glucoamylase performed in the other sample. A third one did not contain any enzymes. The three media were analysed with HPLC and used for shake flask experiments.

The HPLC analysis of the different hydrolysates showed that only the hydrolysate with both the liquefaction and saccharification step contained glucose and 70 g/L wheat flour yielded 48 g/L glucose. The experiment was performed in triplicate in 500 mL shake flasks containing 200 mL medium supplemented with Vogel salts and samples were taken after 24, 48 and 72 hours and analysed in triplicate.

The results of this experiment show that *F. venenatum* can grow equally well in a medium which only consists of wheat hydrolysate with added Vogel salts (11). It therefore is assumed that it uses the starch in solution as a carbon source. The growth is slightly faster in the entirely hydrolysed medium which is presumably caused by the need for the production of amylases in the *Fusarium* to utilise the starch as an energy source. HPLC data (not shown) suggests that even in the medium without any enzymes disaccharides are present which might be utilised at the beginning of the incubation and which might be the reason why no differences in growth can be observed in the first 24 hours. After 72 hours the biomass in all flasks was approximately 7 g/L dry biomass with no noteworthy differences.

1.11 Experiment 2

1.11.1 Aims & Objectives

In order to show that the integration of the processes of the mycoprotein fermentation and the ethanol fermentation is possible, preliminary experiments were conducted to prove that *S. cerevisiae* grows in wheat hydrolysate (section 1.10.3.1). The yeast was also grown in filtrate of the mycoprotein fermentation to observe if growth is existent and to determine if *F. venenatum* produces anything which inhibits the growth of *S. cerevisiae* (section 1.11.3.2).

1.11.2 Experimental Conditions 1.11.3 Results 1.11.3.1 Growth of *S. cerevisiae* in Wheat Hydrolysate Shake flask experiments were performed. For this purpose 100 mL shake flasks were filled with 40 mL medium and grown for 24 h at 250 rpm and 30° C. The flasks were grown and analysed in triplicate. The results of the OD and dry biomass determination are depicted in 2.

The results of this experiment show that *S. cerevisiae* grows equally well in the hydrolysed wheat which was supplemented with the Vogel salts and therefore an integration of the processes is possible. It can be presumed that the wheat hydrolysate contains proteins and other nutrients which are essential for the growth of *S. cerevisiae*, as the medium which only contained glucose and Vogel salts did not promote the same growth.

1.11.3.2 Batch Fermentation of *S. cerevisiae* with Wheat Hydrolysate

In order to show that an integration of the two fermentation processes is possible a fermentation of *S. cerevisiae* with Wheat Hydrolysate was performed. The used fermentation system was DASGIP (Eppendorf) which allowed the execution of four fermentations at the same time. Two fermentations were performed with MYPG as a control and two fermentations with Wheat Hydrolysate (35 g/L flour, 0.5% w/w α-amylase, 1% w/w glucoamylase) supplemented with Vogel salts. The working volume was 800 mL and the fermentation was run for 24 hours, whereas aeration at 0.82 vvm was only present between 8 to 18 hours of fermentation time. The growth of the yeast was monitored by measuring the optical density and determination of the dry biomass.

Both the trend of the optical density and the dry biomass trend of all four fermentations did not show noticeable differences over the time course of the fermentation, 2 and 3.

The HPLC analysis of the samples yielded the following values for the initial glucose concentrations and the final ethanol concentrations. In addition the yield of the conversion of glucose to ethanol was calculated. There yields of the fermentations with WH were slightly higher but in general the trend of both fermentations was similar.

TABLE 4

Analysis of glucose concentration at the beginning of the *S. cerevisiae* fermentation and the maximum ethanol concentration. The yield of the conversion of glucose into ethanol was calculated.

| Fermenter | Glucose [g/L] | Ethanol [g/L] | Yield [%] |
|---|---|---|---|
| 1 | 25.91 | 7.21 | 27.8 |
| 2 | 25.12 | 6.96 | 27.7 |
| 3 | 24.20 | 6.93 | 28.6 |
| 4 | 23.07 | 6.81 | 29.5 |

1.12 Experiment 3

1.12.1 Aims & Objectives

The objective of this experiment was to demonstrate the feasibility of an integrated bioprocess for the production of mycoprotein (*F. venenatum*) and ethanol (using *S. cerevisiae*) using expired feed grade wheat as the growth medium. Previous experiments carried out had suggested that both the *Fusarium* and *Saccharomyces* could be successfully grown on the hydrolysed wheat medium (section 1.10 and 1.11). This experiment built on these findings, attempting to grow the *Fusarium* to a point where sufficient biomass was obtained whilst glucose still remained present in the system to further be utilised by *S. cerevisiae*.

1.12.2 Experimental Conditions 1.12.2.1 Fermentation Process

Experimental conditions are detailed in Table 5.

TABLE 5

Experimental conditions for Experiment 3.

| Parameter | Setting/Value |
|---|---|
| Experimental Conditions | |
| Growth Medium | Hydrolysed wheat (α-amylase & glucoamylase) |
| Medium Volume | 500 mL |
| pH control | Yes |
| Acid | 1 Mol/L Sulphuric Acid |
| Base | 2 Mol/L Ammonium Hydroxide |
| Antifoam | Rapeseed Oil |
| Antifoam Volume | 1 mL |
| Process Parameters | |
| Agitation | 300-900 rpm |
| Aeration | 0.5-0.75 lpm (1-1.5 vvm) |
| pH Setpoint | 6.0 |
| Dissolved Oxygen Setpoint | 30% |
| Cascaded | Yes (for first 20 hours then no cascade, 300 rpm, 0 vvm) |

1.12.3 Sampling & Results

Samples of the culture media were removed immediately post inoculation and then at various time points over the course of the fermentation.

Glucose concentrations were estimated for each of the collected samples using the YSI biochemistry analyser (1.5) as well as the biomass levels of each organism (1.4). As this analysis was carried out in triplicate the reported values were the mean of the three replicates (5 and FIG. 16).

Ethanol quantification in the samples was achieved using the HPLC method (1.6) and the results are also detailed in 6.

1.12.4 Discussion

This experiment demonstrated the ability to integrate the two fermentation processes of interest. The first stage demonstrated the ability to grow the *F. venenatum* to a biomass level in the region of 10 g/L. This biomass was then harvested and the media, still containing in the region of 20 g/L glucose, re-sterilised. This media was then inoculated with *S. cerevisiae* and the growth of this organism subsequently achieved. After a period of approximately 16 hours the culture was starved of oxygen to promote the production of ethanol. The fermentation was continued until a total fermentation time of approximately forty hours was reached, with samples taken at various time points for ethanol quantification using the developed HPLC method (1.6).

Ethanol was not detected during the fermentation of the *Fusarium venenatum* (data not shown). Following inoculation and initial growth of the *S. cerevisiae* ethanol was noted in the samples (approximately 5 g/L), 6.

This demonstrates the feasibility of the approach to integrating the two bioprocesses—*Fusarium venenantum* fermentation for the production of mycoprotein followed by a *S. cerevisiae* fermentation and the production of ethanol using expired feed grade wheat as the growth medium. Optimisation of the process should be carried out to produce the maximum yields of mycoprotein and ethanol from the fermentations to improve the overall process efficiency.

1.12.5 Conclusions

The results have demonstrated that integration of the two bioprocesses for the production of the desired products is possible.

1.13 Experiment 4

A number of fermentations were carried out in an attempt to demonstrate the feasibility of a bioprocess for the production of mycoprotein (as food) and ethanol (as fuel) with *Fusarium venenatum* using expired feed grade wheat as the growth medium.

1.13.1 Aims & Objectives

The objective of this experiment was to demonstrate the feasibility of a bioprocess using *Fusarium venenatum* for the production of both mycoprotein and ethanol using hydrolysed feed grade wheat as a substrate.

Previous carried out experiments had suggested that *Fusarium venenatum* produces either biomass or ethanol depending on the aeration profile used. For this purpose three different aeration profiles were being used in order to determine the differences in biomass and ethanol production. A control fermentation with defined Vogel medium (VM) was used and was aerated throughout the whole course of the fermentation.

The first 20 hours of fermentation time all four fermentations were aerated with the same cascade without oxygen limitation. After 20 hours, fermentation one (VM1) and two (WH2) were further on aerated, whereas in fermentation three (WH3) was oxygen limited by setting the aeration to 0.1 vvm after 20 hours of fermentation. Fermentation four (WH4) the aeration was switched off, which lead to an oxygen starvation. The applied conditions are depicted in Table 6.

TABLE 6

Overview of each fermentation condition used to investigate influence of oxygen limitation.

| Fermentation | Medium | Aeration 1-20 h | Aeration 20-95 h | Oxygen limitation |
|---|---|---|---|---|
| 1 | VM1 | 1-3 vvm (30% DO) | 1-3 vvm (30% DO) | no limitation |
| 2 | WH2 | 1-3 vvm (30% DO) | 1-3 vvm (30% DO) | no limitation |

TABLE 6-continued

Overview of each fermentation condition used to investigate influence of oxygen limitation.

| Fermentation | Medium | Aeration 1-20 h | Aeration 20-95 h | Oxygen limitation |
|---|---|---|---|---|
| 3 | WH3 | 1-3 vvm (30% DO) | 0.1 vvm | Limitation |
| 4 | WH4 | 1-3 vvm (30% DO) | 0 vvm | starvation |

1.13.2 Experimental Conditions

The wheat hydrolysate which was used in fermentation two, three and four was prepared according to 1.3.

1.13.3 Sampling & Results

Samples of the culture media were taken pre inoculation and immediately post inoculation. Samples were then taken twice daily over the course of the fermentation. Details of the samples, their times and the various monitored process parameters were recorded.

Glucose concentrations were estimated for each of the collected samples using the YSI biochemistry analyser (1.5) as well as the biomass levels of each organism (1.4). As this analysis was carried out in triplicate the reported values were the mean of the three replicates. Ethanol quantification in the samples was achieved using the HPLC method described in 1.6.

1.13.3.1 Fermentation 1

Fermentation one was run without oxygen limitation for the *Fusarium venenatum*. This fermentation was used as a control, for which reason Vogel medium with glucose as a carbon source was used as the fermentation medium instead of wheat hydrolysate. The purpose of this was to compare the growth between the different media and determine possible differences. It was expected to yield more biomass in the fermentations without oxygen limitations and not detect considerable amounts of ethanol.

1.13.3.1.1 Experimental Conditions

The experimental parameters utilised for this fermentation process are outlined in Table 7. This fermentation served as a control and was compared to fermentation two.

TABLE 7

Experimental conditions for fermentation one.

| Parameter | Setting/Value | |
|---|---|---|
| Experimental Conditions | | |
| Growth Medium | Vogel medium with 45 g/L glucose | |
| Medium Volume | 800 mL | |
| pH control | Yes | |
| Acid | 2 Mol/L sulphuric acid | |
| Base | 25% v/v ammonia solution | |
| Antifoam | Rapeseed Oil | |
| Antifoam Volume | 1 mL (and as required) | |
| Process Parameters | | |
| | Phase 1 (0-20 h) | Phase 2 (20-95 h) |
| Agitation | 300-1200 rpm | 300-1200 rpm |
| Aeration | 0.8-2.4 slpm (1-3 vvm) | 0.8-2.4 slpm (1-3 vvm) |
| pH Setpoint | 6 | 6 |
| Dissolved Oxygen Setpoint | 30% | 30% |
| Cascaded | Yes | Yes |

1.13.3.1.2 Results

In fermentation one most of the biomass was produced in the first 20 hours of the fermentation where it reached levels of 22 g/L of dry biomass. The maximum dry biomass was reached at the end of the fermentation after 96 hours, when 25 g/L of dry biomass were present. No ethanol was detected throughout the course of the fermentation. After 20 hours only 0.4 g/L of glucose of the initial 43.5 g/L were available for the *Fusarium*. The trends of the dry biomass, ethanol and glucose levels can be seen in 7, 8 and 9.

1.13.3.1.3 Conclusions

As expected, no ethanol was produced in this fermentation, while it yielded large amounts of biomass of 25 g/L. The biomass production could probably be increased by feeding substrate into the fermenter and harvesting biomass. With increasing biomass an increased viscosity can be observed, which impedes mixing and oxygen transfer. Therefore harvesting biomass can be beneficial for the production of biomass.

1.13.3.2 Fermentation 2

The substrate used in fermentation two was wheat hydrolysate supplemented with Vogel salts which was also used in fermentation three (1.13.3.3) and four (1.13.3.4). It was not oxygen limited over the course of the fermentation. This fermentation was compared to Fermentation one in order to give conclusions about differences in yield between the used media. It was expected to obtain closer results from this fermentation compared to fermentation one with Vogel medium.

1.13.3.2.1 Fermentation Process

In fermentation two wheat hydrolysate was used as a fermentation medium. The set point for the dissolved oxygen was set to 30%. The further experimental conditions are detailed in Table 8.

TABLE 8

Experimental conditions for fermentation two.

| Parameter | Setting/Value | |
|---|---|---|
| Experimental Conditions | | |
| Growth Medium | Wheat Hydrolysate with Vogel salts | |
| Medium Volume | 800 mL | |
| pH control | Yes | |
| Acid | 2 Mol/L sulphuric acid | |
| Base | 25% v/v ammonia solution | |
| Antifoam | Rapeseed Oil | |
| Antifoam Volume | 1 mL (and as required) | |
| Process Parameters | | |
| | Phase 1 (0-20 h) | Phase 2 (20-95 h) |
| Agitation | 300-1200 rpm | 300-1200 rpm |
| Aeration | 0.8-2.4 slpm (1-3 vvm) | 0.8-2.4 slpm (1-3 vvm) |
| pH Setpoint | 6 | 6 |
| Dissolved Oxygen Setpoint | 30% | 30% |
| Cascaded | Yes | Yes |

1.13.3.2.2 Results

The dry biomass, ethanol and glucose trends of the fermentation with wheat hydrolysate and no oxygen limitation are shown in 7, 8 and 9. The maximum dry biomass concentration of 21 g/L was reached after 44 hours although glucose levels reached 0.13 g/L after 27 hours. Ethanol was only present after 20 hours but was possibly used as a carbon source afterwards and no ethanol could be detected in the further course of the fermentation.

1.13.3.2.3 Conclusions

The fermentation yielded approximately the same biomass levels as the first fermentation. The initial glucose levels were lower which explains the difference in reached biomass levels. Furthermore ethanol was not detected throughout the fermentation with the exception of the 20 hour sample.

1.13.3.3 Fermentation 3

In fermentation three the effect of oxygen limitation on the ethanol production was investigated. The results were compared to the previous fermentations, in particularly to the fermentation with oxygen starvation conditions (fermentation four). It should give further insight into the influence of the presence of oxygen on ethanol production.

1.13.3.3.1 Experimental Conditions

The experimental conditions are detailed in Table 9. Wheat hydrolysate supplemented with Vogel salts was used as a fermentation medium and after a 20 hour phase of no oxygen limitation the aeration was set to 0.1 vvm in order to obtain oxygen limiting conditions.

TABLE 9

Experimental conditions for fermentation three.

| Parameter | Setting/Value | |
|---|---|---|
| Experimental Conditions | | |
| Growth Medium | Wheat Hydrolysate with Vogel salts | |
| Medium Volume | 800 mL | |
| pH control | Yes | |
| Acid | 1M sulphuric acid | |
| Base | 25% v/v ammonia solution | |
| Antifoam | Rapeseed Oil | |
| Antifoam Volume | 1 mL (and as required) | |
| Process Parameters | | |
| | Phase 1 (0-20 h) | Phase 2 (20-95 h) |
| Agitation | 300-1200 rpm | 300 rpm |
| Aeration | 0.8-2.4 slpm (1-3 vvm) | 0.08 slpm (0.1 vvm) |
| pH Setpoint | 6 | 6 |
| Dissolved Oxygen Setpoint | 30% | No setpoint |
| Cascaded | Yes | No |

1.13.3.3.2 Results

In fermentation three the starting glucose concentration was 34.5 g/L and glucose was depleted from the fermentation medium after 27 hours. The produced biomass was much lower than in the fermentations under no oxygen limitation (fermentation 1 and 2) with a maximum value of 11 g/L which was detected after 75 hours of fermentation time. Ethanol production reached its highest value of 4.8 g/L after 44 hours. The trends for the substrate and products over the course of the fermentation can be seen in 7, 8 and 9.

1.13.3.3.3 Conclusions

In fermentation three (under oxygen limiting conditions) the major amount of ethanol was produced during the first 24 h under oxygen limiting conditions. During the later stages of the fermentation the ethanol concentration decreased, suggesting it was being utilised as a carbon source by the organism.

1.13.3.4 Fermentation 4

In fermentation four it was studied how much oxygen starvation of the organism after an initial growth phase of 20 hours would affect the amount of produced ethanol. It was expected to get lower levels of biomass during the phase of oxygen starvation but a considerable increase in the production of ethanol.

1.13.3.4.1 Experimental Conditions

The experimental conditions employed for fermentation four are detailed in Table 10. Wheat hydrolysate was used as a fermentation medium and after 20 hours of no oxygen limitation the aeration set to 0 vvm in order to starve the *Fusarium* of oxygen.

TABLE 10

Experimental conditions for fermentation four.

| Parameter | Setting/Value | |
|---|---|---|
| Experimental Conditions | | |
| Growth Medium | Wheat hydrolysate with Vogel salts | |
| Medium Volume | 800 mL | |
| pH control | Yes | |
| Acid | 1M sulphuric acid | |
| Base | 2M ammonium hydroxide | |
| Antifoam | Rapeseed Oil | |
| Antifoam Volume | 1 mL (and as required) | |
| Process Parameters | | |
| | Phase 1 (0-20 h) | Phase 2 (20-95 h) |
| Agitation | 300-1200 rpm | 300 rpm |
| Aeration | 0.8-2.4 slpm (1-3 vvm) | 0 slpm (0 vvm) |
| pH Setpoint | 6 | 6 |
| Dissolved Oxygen Setpoint | 30% | No setpoint |
| Cascaded | Yes | No |

1.13.3.4.2 Results

Samples were taken at regular intervals over the course of the fermentation process. Fermentation four had a starting glucose concentration of 32.5 g/L and was depleted after 27 hours. The dry biomass also peaked after 27 hours (10 g/L). Ethanol concentrations were at its highest at the end of the fermentation and reached 11.7 g/L. The detailed course of the determined parameters is depicted in 7, 8 and 9.

1.13.3.4.3 Conclusions

The results from this fermentation suggest that oxygen starvation is advantageous for ethanol production. After switching to the aeration off biomass did not increase anymore but decreased until the end of the fermentation. Although the biomass concentration decreased, ethanol continued to increase during the starvation phase of the fermentations and reached its highest levels at the end of the of the process. Glucose was depleted after 27 hours, it is possible that other oligosaccharides present in the wheat hydrolysate were used for the production of ethanol

1.13.3.5 Experiment 4 Conclusions

In order to understand the effect of the different aeration profiles on biomass and ethanol production, the process parameters of the fermentations were compared. In 7 it can be seen that It is very clear that the oxygen limited and starved fermentations produce significantly less dry biomass than the oxygen unlimited fermentations. However, during the aerated phase of the wheat hydrolysate fermentations (first 20 h), the growth rate is approximately the same (0.34 g/L·h), showing reproducibility of the process.

Furthermore the production of the second product, ethanol, in the different fermentations was investigated. In these fermentations it was observed that oxygen starvation leads to a significantly increased ethanol production (8) which is significantly different from the ethanol levels reached in the other fermentations. After 20 hours all the fermentations carried out with wheat hydrolysate (Fermentation 2-4) showed the same amount of ethanol which was different from the fermentation carried out with Vogel medium (Fermentation 1). Only the oxygen starved fermentation showed ethanol in the fermentation medium at the end of the fermentation.

In 8 the glucose concentrations over the fermentation course are depicted. The starting glucose concentrations in the wheat hydrolysate were slightly lower than in the Vogel medium, however the consumption rate in all fermentations was approximately 0.40 g/L*h. Biomass and ethanol yields on glucose were calculated during the aerated phase (Table 11) and during the whole process time (Table 12) in order to attain a better comparison of the fermentations.

TABLE 11

Process yields during aerated phase of fermentation (first 20 h) for the conversion of glucose into biomass and ethanol, as well as biomass and ethanol productivity.

| Fermentation | $Y_{DCW/Glc}$ [%] | $Y_{EtOH/Glc}$ [%] | $P_{DCW}$ [$g_{DCW}$/L*h] | $P_{EtOH}$ [$g_{EtOH}$/L*h] |
|---|---|---|---|---|
| VM1 | 44.69 | 0.00 | 0.96 | 0.00 |
| WH2 | 28.89 | 10.55 | 0.39 | 0.14 |
| WH3 | 22.98 | 20.68 | 0.30 | 0.27 |
| WH4 | 25.49 | 19.59 | 0.34 | 0.26 |

Abbreviations: VM1: Vogel medium, no oxygen limitation;
WH2: wheat hydrolysate, no oxygen limitation,
WH3: wheat hydrolysate, oxygen limitation;
WH4: wheat hydrolysate, oxygen starvation.
$Y_{DCW/Glc}$: yield of biomass on glucose,
$Y_{EtOH/Glc}$: yield of ethanol on glucose,
$P_{DCW}$: Biomass productivity,
$P_{EtOH}$: Ethanol productivity As expected, during the aerated phase fermentation one (VM1) showed a higher conversion of biomass on glucose than in the fermentations using wheat hydrolysate (fermentation two-four). The biomass productivity was also a factor of 3 higher in Vogel medium (fermentation one, VM1), indicating that glucose is more efficiently converted into biomass in the defined medium (VM). However, ethanol production is favoured in the wheat hydrolysate medium (fermentation two-four), even during this phase of the process.

In Table 12 it can be seen, that although the biomass levels during fermentation two were lower than in fermentation one, the overall yield of the conversion of glucose into biomass is similar (—50%). Furthermore, the highest conversion of glucose into ethanol and the highest ethanol productivity is under oxygen starvation conditions (WH4). This means that these conditions favoured ethanol production compared to biomass production (highest under no oxygen limitation conditions).

TABLE 12

Total process yields for the conversion of glucose into biomass and ethanol, as well as biomass and ethanol productivity (overall process time 96 h).

| Fermentation | $Y_{DCW/Glc}$ [%] | $Y_{EtOH/Glc}$ [%] | $P_{DCW}$ [$g_{DCW}$/L*h] | $P_{EtOH}$ [$g_{EtOH}$/L*h] |
|---|---|---|---|---|
| VM1 | 50.47 | 0.00 | 0.16 | 0.00 |
| WH2 | 49.34 | 0.00 | 0.23 | 0.00 |
| WH3 | 21.92 | 16.57 | 0.08 | 0.06 |
| WH4 | 11.33 | 36.16 | 0.04 | 0.12 |

Abbreviations: VM1: Vogel medium, no oxygen limitation;
WH2: wheat hydrolysate, no oxygen limitation,
WH3: wheat hydrolysate, oxygen limitation;
WH4: wheat hydrolysate, oxygen starvation.
$Y_{DCW/Glc}$: yield of biomass on glucose,
$Y_{EtOH/Glc}$: yield of ethanol on glucose,
$P_{DCW}$: Biomass productivity,
$P_{EtOH}$: Ethanol productivity As well as monitoring the substrate and product concentrations, further process parameters were monitored. Depicted in is the dissolved oxygen concentration which gives an insight in oxygen levels in the fermentation medium. Fermentation three and four were limited in oxygen after 20 hours, when the aeration was decreased.

1.13.3.6 Conclusions

The results shown in this report demonstrate that the hypothesis of producing biomass as well as ethanol with *Fusarium venenatum* from feed grade wheat hydrolysate is feasible. Furthermore, it is also demonstrated for the first time that process control (i.e. manipulation aeration conditions) favours either biomass production (no oxygen limitation conditions) or ethanol production (oxygen starvation conditions). Process optimisation can be done in such a way that aeration is present for long enough to obtain a sufficient biomass concentration, before the organism can be starved of oxygen and therefore the fermentation of ethanol can start.

A process with oxygen starving conditions seems preferable for a high ethanol yield. Even with very low biomass levels a substantial amount of ethanol can be produced (and is favoured) in the absence of oxygen (fermentation four). It is possible to harvest large amounts of biomass before the start of ethanol production phase (first 20 h of the process). Therefore, by manipulating the process conditions it is possible to adjust the process in order to obtain the desired product.

Using a single organism for the production of both products (biomass and ethanol) has big economical and downstream processing advantages. A production process can be adapted according to the demand of mycoprotein (biomass) or ethanol by having a prolonged or shortened aerated phase. The process could be improved furthermore by harvesting biomass and feeding more wheat hydrolysate into the fermentation. Producing ethanol without the necessity of aeration would reduce production costs substantially and would therefore influence the overall process economy.

REFERENCES

Cardona C A, Sánchez Ó J: Fuel ethanol production: Process design trends and integration opportunities. *Bioresour Technol* 2007, 98:2415-2457.

Finn B, Harvey L M, McNeil B: Near-infrared spectroscopic monitoring of biomass, glucose, ethanol and protein content in a high cell density baker's yeast fed-batch bioprocess. *Yeast* 2006, 23:507-517

The invention claimed is:

1. An integrated method or system for producing and isolating mycoprotein produced by *Fusarium venenatum* and ethanol from hydrolysed starch feedstock, the method comprising the steps of:
   a) providing an aqueous fermentable broth comprising a hydrolysed starch feedstock;
   b) a first fermentation step comprising fermenting at least a portion of the aqueous fermentable broth with *Fusarium venenatum* in order to obtain mycoprotein produced by *Fusarium venenatum* respectively and partially fermented broth;
   c) separating the mycoprotein produced by *Fusarium venenatum* from the partially fermented broth;
   d) a second fermentation step comprising fermenting at least a portion of the partially fermented broth, optionally with a portion of unfermented aqueous fermentable broth, with a micro-organism(s) in order to obtain ethanol and a spent fermentation residue; and
   e) isolating the ethanol from the spent fermentation residue.

2. The method or system according to claim 1, wherein the mycoprotein and ethanol are produced by aerobic digestion and anaerobic fermentation respectively using *Fusarium venenatum*.

3. The method or system according to claim 1, wherein the operating conditions are controlled in each of the steps to preferentially favour mycoprotein produced by *Fusarium venenatum*, or ethanol.

4. The method or system according to claim 1, wherein mycoprotein produced by *Fusarium venenatum* is fully isolated from the first fermentation step and the second fermentation step to obtain ethanol is carried out using a microorganism other than *Fusarium venenatum*.

5. The method or system according to claim 1, wherein *Fusarium venenatum* is used for both the mycoprotein and ethanol fermentation steps.

6. The method or system according to claim 1, wherein mycoprotein produced by *Fusarium venenatum* and ethanol are produced in a single fermenter where the operating conditions are controlled to produce a desired mixture ratio of mycoprotein produced by *Fusarium venenatum* and ethanol.

7. The method or system according to claim 1, wherein the initial substrate is a grain material and the integrated process additionally produces a co-product with increased protein content which could be utilised as a source of livestock feed.

8. The method or system according to claim 6, wherein the operating conditions and resulting production mixture ratio or rate of mycoprotein produced by *Fusarium venenatum* and ethanol is altered to match phasing of energy provision or cost taking into account the higher energy intensity of fermentation under aerobic conditions required to increase the production rate of mycoprotein produced by *Fusarium venenatum*.

9. The method or system according to claim 3, wherein the mycoprotein produced by *Fusarium venenatum* is fully or partially isolated between the 2 fermentation steps.

* * * * *